United States Patent
Cesaroni

(10) Patent No.: US 10,238,532 B2
(45) Date of Patent: Mar. 26, 2019

(54) BODY TEMPERATURE CONTROLLING SYSTEM

(75) Inventor: Anthony J. Cesaroni, Sarasota, FL (US)

(73) Assignee: Cesaroni Technology Incorporated, Sarasota, FL (US)

( * ) Notice: Subject to any disclaimer, the term of this patent is extended or adjusted under 35 U.S.C. 154(b) by 2115 days.

(21) Appl. No.: 12/137,414

(22) Filed: Jun. 11, 2008

(65) Prior Publication Data
US 2008/0306433 A1  Dec. 11, 2008

Related U.S. Application Data

(60) Provisional application No. 60/943,222, filed on Jun. 11, 2007.

(51) Int. Cl.
*A61F 7/00* (2006.01)
*A61F 7/02* (2006.01)

(52) U.S. Cl.
CPC ........ *A61F 7/02* (2013.01); *A61F 2007/0063* (2013.01); *A61F 2007/0069* (2013.01); *A61F 2007/0075* (2013.01); *A61F 2007/0234* (2013.01)

(58) Field of Classification Search
CPC .... A61F 7/00; A61F 7/02; A61F 7/007; A61F 2007/0075; A61F 2007/0076; A61F 2007/0069; A61F 2007/006; A61F 7/0063; A61F 7/0064; A61F 7/0069; A61F 7/0258; A61F 2007/0058; A61F 2007/0064; A61F 2007/0065; A61F 2007/0059

USPC ........................................... 607/98, 108–111
See application file for complete search history.

(56) References Cited

U.S. PATENT DOCUMENTS

| | | | | |
|---|---|---|---|---|
| 3,295,522 A | * | 1/1967 | Johnson | A62B 18/00 128/201.23 |
| 3,302,414 A | * | 2/1967 | Sudmeier | B60H 1/00478 136/204 |
| 4,002,040 A | * | 1/1977 | Munters | F24F 5/0007 62/121 |
| 4,228,848 A | * | 10/1980 | Wadkinson, Jr. | F28D 7/106 165/134.1 |
| 4,691,762 A | * | 9/1987 | Elkins | A61F 7/02 165/46 |
| 5,243,706 A | | 9/1993 | Frim et al. | |
| 5,564,124 A | * | 10/1996 | Elsherif | A41D 13/0025 2/457 |
| 5,655,374 A | * | 8/1997 | Santilli | A41D 13/1218 2/905 |
| 5,785,117 A | | 7/1998 | Grinbergs | |
| 5,938,693 A | * | 8/1999 | Carminucci | A61F 7/0085 607/104 |
| 5,967,225 A | | 10/1999 | Jenkins | |
| 6,189,327 B1 | * | 2/2001 | Strauss | A41D 13/0025 62/259.3 |

(Continued)

OTHER PUBLICATIONS

International Search Report for International application No. PCT/US2008/066594, International filing date is Jun. 11, 2008.

*Primary Examiner* — Jenna Zhang
(74) *Attorney, Agent, or Firm* — Boyle Fredrickson, S.C.

(57) ABSTRACT

The present invention is directed to a body temperature controlling system comprising at least one member receiving a flow of gas from at least one blower in communication with said at least one member, said at least one member directing said flow of gas onto a wearer thereof.

37 Claims, 32 Drawing Sheets

(56) References Cited

U.S. PATENT DOCUMENTS

| | | |
|---|---|---|
| 6,751,963 B2 | 6/2004 | Navedo et al. |
| 6,855,410 B2 | 2/2005 | Buckley |
| 6,915,641 B2 * | 7/2005 | Harvie ............... A41D 13/0051 62/259.3 |
| 6,993,930 B2 * | 2/2006 | Blackstone ........ A41D 13/0025 601/15 |
| 7,124,593 B2 | 10/2006 | Feher |
| 8,128,675 B2 * | 3/2012 | Nahhas .................. A61F 7/007 2/400 |
| 2002/0157815 A1 * | 10/2002 | Sutter .................... F28D 7/022 165/154 |
| 2003/0098143 A1 * | 5/2003 | Winkle ................ A41D 13/005 165/46 |
| 2004/0159109 A1 * | 8/2004 | Harvie ............... A41D 13/0051 62/3.5 |
| 2005/0000231 A1 * | 1/2005 | Lee ................... A41D 13/0025 62/3.5 |
| 2006/0191270 A1 * | 8/2006 | Warren ................ A41D 13/005 62/3.3 |
| 2007/0283961 A1 * | 12/2007 | Hsieh .................. A62B 17/006 128/205.29 |
| 2008/0027383 A1 * | 1/2008 | Nahhas .................. A61F 7/007 604/113 |
| 2009/0308082 A1 * | 12/2009 | Monk .................. A41D 13/005 62/3.3 |

\* cited by examiner

BODY TEMPERATURE CONTROLLING SYSTEM

CROSS-REFERENCE TO RELATED APPLICATIONS

This application claims priority from U.S. Provisional Patent Application Ser. No. 60/943,222, filed on Jun. 11, 2007, the entirety of which is expressly incorporated by reference herein.

STATEMENT REGARDING FEDERALLY SPONSORED RESEARCH OR DEVELOPMENT

This invention was made with United States government support through contract number H92222-06-P-0047, under the United States Department of Defense. The United States may have certain rights in this invention.

FIELD OF THE INVENTION

The present invention relates to a temperature controlling system, in particular, a body temperature controlling system.

BACKGROUND OF THE INVENTION

Military ground mobility vehicles often operate in areas of high heat with no environmental conditioning systems for cooling the individual soldier or critical vehicle electronic systems. It is well documented that working in extremely hot environments leads to reduced physical and cognitive performance. Typical vehicle climate control systems are large refrigerant-based systems that are not man portable.

Portable cooling methods and/or systems would be beneficial not only for military applications but also, for example, in sports (e.g. cooling athletes during training and competition), industrial and medical applications.

Currently, there are a number of potential cooling methods and/or systems as well as application methods but each have there own disadvantages. The following is a list of some of these examples:
- refrigeration cycle based cooling
- vortex cooling
- thermoelectric based cooling
- liquid cooled vests
- passive (phase change) vests
- air cooled vests With respect to refrigeration cycle based cooling, Rankine cycle refrigeration is an efficient method of heating and cooling. At least one variation has been deployed in combat operations. The system however does not support dismounted operations and requires integration into the vehicle's air-conditioning system or an air-conditioning system must be retrofitted to the vehicle if it is not so equipped.

With respect to vortex cooling, the Ranque-Hilsch vortex tube is a simple device that has no moving parts. Vortex tubes are popular in the industry for spot cooling of machinery, processes and electronic equipment. A number of manufacturers have incorporated them into cooling garments as well as respiration systems and although simple and very effective, they do require high volumes of compressed air in order to operate. A typical vortex tube based personnel cooling system may consume from 10 to 25 SCFM of air at 100 psi for example. This restricts mobility to a fixed compressed air source or requires compressed air to be carried which is not practical in most cases due to increased mass and short operational duration.

With respect to thermoelectric devices (TEDs), TEDs have been used extensively in cooling and heating applications since their commercial inception in the 1950's. Typical applications include compact refrigerators/warmers, water coolers, electronic cooling and temperature references as well as biomedical systems. Unfortunately the current generation of TEDs is relatively inefficient when compared to Rankin cycle refrigeration systems on a power/heat in/heat out basis or coefficient of performance (COP).

With respect to liquid cooled vests, these vests have found extensive use in a variety of personnel cooling applications over the years. The cooling sources are typically refrigeration systems or thermal storage (ice water) based but there have been some examples utilizing TED s. Refrigeration and thermal based systems can limit their mobility in mass and/or space sensitive applications. Traditional TED based configurations have been power intensive primarily due to low efficiency and high interface resistance and losses. Because this is a form of thermal contact cooling, the device must operate with a cooling temperature below about 37° C. (98° F.). This higher $\Delta T$ in relationship to ambient temperature can increase power demands when using this approach.

With respect to passive cooled vests, these vests have found limited use for personnel cooling in certain military environments. The vest contains packages of eutectic salts or parafinitic hydrocarbons which absorb heat and cool by phase change and thermal storage. They are typically designed to operate at about 21° C. (65° F.). This temperature range is advantageous as it provides good recharging characteristics using only ice water or refrigeration while minimizing vasoconstriction that would further increase cooling resistance as excessively cold temperatures are not directly applied to the subject. The user, however, must have access to a cold source as previously described in order to thermally recharge the vest. This would greatly limit its effectiveness as a portable garment.

With respect to air-cooled vests, certain designs of air cooled vests work primarily by removing heat trapped under the user's outerwear. This is effective with heavy or insulated outerwear or in cases where solar loads may be high, providing that the ambient air temperature is below or not significantly above body temperature. The user of the air-cooled vest must drink water constantly to keep from becoming dehydrated. Some commercial examples of air-cooled vests utilize vortex cooling tubes discussed above and other examples of air cooled vests employ controlled release and expansion of compressed carbon dioxide to provide cooling. This approach is interesting as $CO_2$ also acts as a topical vasodilator reducing the body's resistance to cooling. Unfortunately, high concentrations of $CO_2$ can form carbonic acid when contacting the skin or mucus membranes. Hypoxia and hypercapnia are also potential hazards when operating this type of system in a poorly ventilated or enclosed area. Notably, hypercapnia has been shown to increase the core cooling rate in humans.

There is a need for temperature controlling methods and/or systems that mitigate and obviate at least one or more of the disadvantages of the prior art systems.

SUMMARY OF THE INVENTION

In accordance with an aspect, there is provided a body temperature controlling system comprising:
at least one member receiving a flow of gas from at least one blower in communication with said at least one member, said at least one member directing said flow of gas onto a wearer thereof.

In accordance with another aspect, said at least one member is of a suitable size, shape, and/or configuration capable of controlling the wearer's body temperature.

In accordance with another aspect, said at least one member is porous. In accordance with another aspect, wherein said at least one member comprises a frame. In accordance with another aspect, the frame is covered with a porous material. In accordance with yet another aspect, the porous material is a fabric. In accordance with another aspect, the fabric comprises a mesh-like fabric.

In accordance with another aspect, the frame comprises a 3-dimensional porous material having a generally flexible structure. In accordance with another aspect, the 3-dimensional porous material comprises a 3-dimensional mesh-like material. In accordance with another aspect, the frame comprises a stand-off material.

In accordance with another aspect, said at least one member is at least one conduit. In accordance with another aspect, said at least one conduit comprises a plurality of conduits, said conduits having at least one feed conduit and at least one return conduit. In accordance with another aspect, said at least one conduit is a counter-flow conduit. In accordance with another aspect, said at least one conduit comprises at least one multilumen conduit. In accordance with another aspect, said at least one multilumen conduit comprises at least one feed conduit and at least one return conduit. In accordance with another aspect, said at least one multilumen conduit is co-axial. In accordance with another aspect, at least one main feed conduit in communication with said at least one feed conduit and at least one main return conduit in communication with said at least one return conduit. In accordance with another aspect, said at least one conduit is at least one of a panel-like conduit, tube, duct, channel, and 3-dimensional porous material. In accordance with another aspect, the panel-like conduit comprises a suitable width so as to occupy any portion of the system.

In accordance with another aspect, at least one of said at least one conduit comprises a wall having any of porosity, openings, and vents.

In accordance with another aspect, the system further comprises at least one regenerative heat exchanger in communication with said at least one member and said at least one blower.

In accordance with another aspect, the system further comprises a manifold comprising at least one regenerative heat exchanger and said at least one blower, said manifold in communication with said at least one member. In accordance with another aspect, said manifold is capable of being worn around the waist. In accordance with another aspect, said at least one heat exchanger is at least one cross-over heat exchanger. In accordance with another aspect, said at least one blower comprises a feed blower and a return blower.

In accordance with another aspect, the system further comprises at least one nebulizer. In accordance with another aspect, the system further comprises at least one thermoelectric device. In accordance with another aspect, the system further comprises said heat exchanger and/or said at least one conduit are in communication with said at least one nebulizer. In accordance with another aspect, the said heat exchanger and/or said at least one conduit are in communication with said at least one thermoelectric device. In accordance with another aspect, the at least one thermoelectric device is detachable. In accordance with another aspect, the at least one thermoelectric device is reversibly operable so as to provide either heating or cooling. In accordance with another aspect, the at least one nebulizer and said at least one thermoelectric device are operable in conjunction with one another. In accordance with another aspect, the at least one nebulizer and said at least one thermoelectric device are automatically adjusted using a thermostat.

In accordance with another aspect, the system further comprises a garment. In accordance with another aspect, the system is self-contained.

In accordance with another aspect, the at least one member is arranged such that the wearer is suitably covered to control body temperature.

In accordance with another aspect, there is provided a body temperature controlling system comprising:

at least one conduit in communication with the body of a wearer to control body temperature;

a blower in communication with said at least one conduit to provide a flow of gas through said at least one conduit, the gas flowing from the conduit to the body;

a regenerative heat exchanger in communication with said at least one conduit and said blower.

In accordance with another aspect, at least one of said at least one conduit being a counter-flow conduit.

In accordance with another aspect, there is provided a body temperature controlling system comprising:

at least one conduit in communication with the body of a wearer to control body temperature, at least one of said at least one conduit being a counter-flow conduit; and a blower in communication with said at least one conduit to provide a flow of gas through said at least one conduit, the gas flowing from the conduit to the body.

In accordance with another aspect, the system further comprises a regenerative heat exchanger in communication with said at least one conduit and said blower.

In accordance with an aspect, there is provided a body temperature controlling system comprising:

at least one conduit in communication with the body of a wearer to control body temperature, said at least one conduit having at least one gas inlet and at least one gas outlet;

a blower in communication with the gas inlet of said at least one conduit to provide a flow of gas through said at least one conduit, the gas flowing from the conduit to the body;

a regenerative heat exchanger in communication with said blower and the gas inlet and the gas outlet of said at least one conduit to transfer heat from the gas which exits the gas outlet to the gas which enters the gas inlet.

In accordance with another aspect, at least one of said at least one conduit being a counter-flow conduit.

In accordance with an aspect, there is provided a body temperature controlling system comprising:

at least one conduit in communication with the body of a wearer to control body temperature, said at least one conduit having a gas inlet and a gas outlet and at least one of said at least one conduit being a counter-flow conduit; and a blower in communication with the gas inlet of said at least one conduit to provide a flow of gas through said at least one conduit, the gas flowing from the conduit to the body.

In accordance with another aspect, the system further comprises a regenerative heat exchanger in communication with said blower and the gas inlet and the gas outlet of said at least one conduit to transfer heat from the gas which exits the gas outlet to the gas which enters the gas inlet.

In accordance with other aspects, the body temperature controlling system described above in combination with at least one garment.

In a further aspect, the system is coupled to said at least one garment.

In accordance with other aspects of the system described above, wherein the counter-flow conduit is a multi-lumen conduit, for example, and without being limited thereto, a co-axial conduit.

In accordance with other aspects of the system described above, wherein the conduit is porous and/or comprises openings in wall(s) therein.

In accordance with other aspects of the system described above, the gas entering the system contains droplets of liquid. The droplets of liquid may be produced using a nebulizer.

In accordance with further aspects of the system described above, the gas is further cooled with a thermoelectric device in communication with the conduit(s).

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Certain embodiments of the present invention will now be described more fully with reference to the accompanying drawings, wherein like numerals denote like parts.

DETAILED DESCRIPTION OF CERTAIN EMBODIMENTS

An embodiment is directed to a body temperature controlling system. Typically, the system is lightweight and has high mobility, and is generally used to control the temperature of the wearer and, for example, to maintain a comfortable body temperature of the wearer. Such a garment may be used for military applications, but may also be used, for example, in sports (e.g. for cooling athletes during training and competition), industrial and medical applications.

In specific embodiments, the system is pre-assembled, self-contained and easily donned by the wearer, in particular, by soldiers with their operational gear. The system may also be integrated with other gear that a soldier wears (for example, body armor, or chemical/biological protective equipment). In other embodiments, the power supply of the system is rechargeable, typically by the wearer, and is compatible with existing power systems such as, for example, vehicle power systems during military mounted operations.

Figure 1:
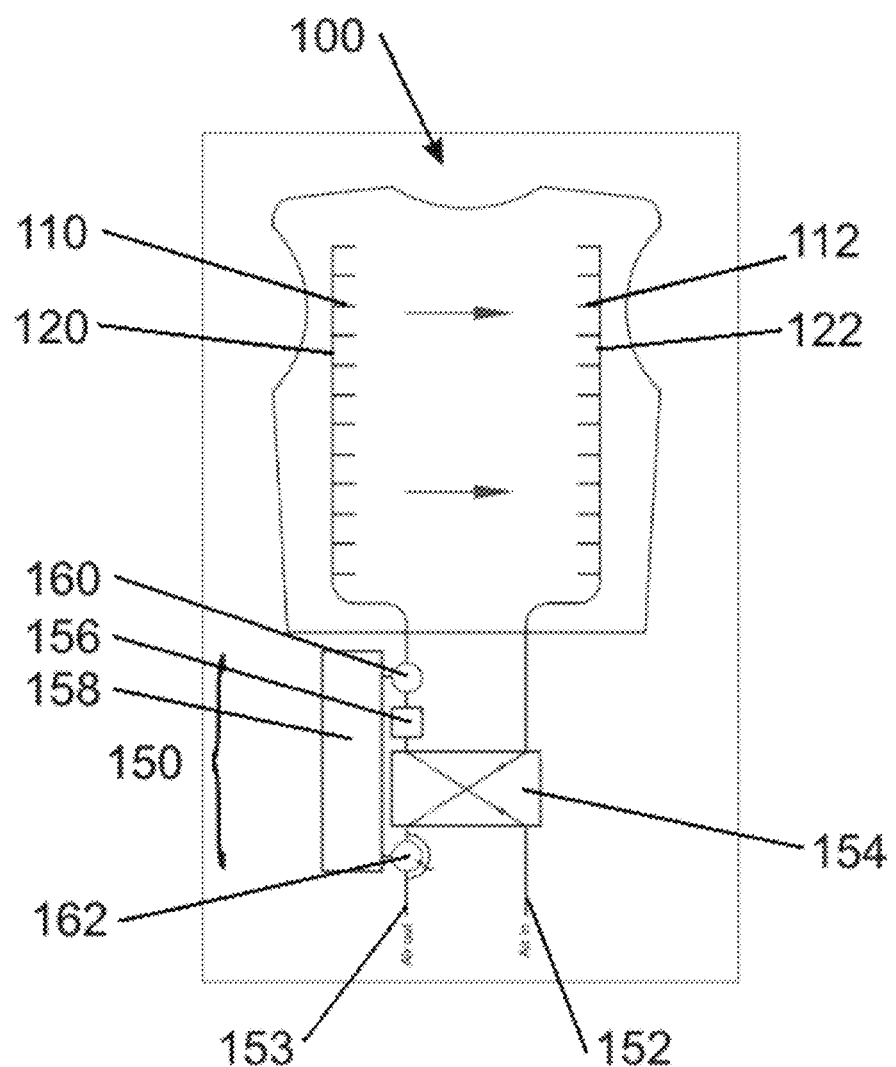
FIG. 1 shows a schematic of one embodiment of a body temperature controlling system.

An embodiment of a body temperature controlling system is shown schematically in FIG. 1 and indicated generally by numeral 100. The system 100 comprises feed conduits 110 coupled to and in communication with main feed conduit 120, which operate together with return conduits 112 coupled to and in communication with main return conduit 122. The conduits 110 and 112 are microtubes and are arranged such that the torso of the wearer is suitably covered by several conduits 110 and 112. The main feed conduit 120 and the main return conduit 122 are in communication with a manifold 150. The manifold 150 comprises feed blower 152, return blower 153 and a cross-over heat exchanger 154. The purpose of this heat exchanger 154 is to pre-cool the warm incoming air with exhaust air that has already been cooled in the internal environment of the system 100. The manifold 150 also comprises an ultrasonic nebulizer 156 and a thermoelectric device (TED) 158. The TED 158 has a TED cold side 160 and a TED hot side 162 and, in the embodiment shown, the feed conduit 120 is in communication with the TED cold side 160 for cooling purposes. Nebulizer 156 provides additional evaporative cooling through the addition of small amounts of supplemental water added to the air cycle via high frequency ultrasonic atomization. This results in the production of an aerosol of extremely fine, micron sized droplets with high surface area and mobility. Very compact, portable ultrasonic nebulizers for personal use are commercially available and require low levels of power to operate, such as standard AA batteries. A power source may be provided to supply power to the various components of manifold 150.

In operation, as depicted schematically in FIG. 1, air is drawn into the manifold 150 by the feed blower 152, where the air is cooled sequentially by the heat exchanger 154, the nebulizer 156, and the TED cold side 160. This cooled air is blown from the main feed conduit 120 via the feed conduits 110 over the torso of the wearer to the main return conduit 122 via the return conduits 112, as drawn by the return blower 153. The return air is passed through the heat exchanger 154 to cool incoming air. This air, which is still cooler than ambient, can be exhausted through the heat exchanger at the TED hot side 162 to remove any heat generated by the TED 158, thereby increasing the efficiency of the system.

FIG. 2 shows a front perspective view of a further embodiment of a body temperature controlling system, which is indicated generally by numeral 200. Feed conduits 110 and return conduits 112 of the embodiment of FIG. 1 are effectively combined into conduits 214 carrying both feed and return flows. Similarly, the main feed conduit 120 and main return conduit 122 of FIG. 1 are effectively combined into two single counter-flow conduits each carrying both a feed and a return flow, namely right main conduit 224 and left main conduit 226. The specific cross-sectional geometries of conduits 214 and main conduits 224 and 226 will be described below using FIGS. 4, 5 and 6. The main conduits 224 and 226 are L-shaped, and have respective first portions 234 and 236 parallel to the vertical axis of the body of the wearer and are spaced apart from one another. Second portions 238 and 240 of the main conduits 224 and 226, respectively, are perpendicular to the vertical axis of the body of the wearer, wherein one main conduit 224 continues around the waist of one side of the wearer via second portion 238 while the other main conduit 226 continues around the waist of the other side of the wearer via the second portion 240. Ends 242 and 244 of the main conduits 224 and 226, respectively, terminate at one end 246 of a supply conduit 248, and the main conduits 224 and 226 are thereby in communication with the supply conduit 248. The system 200 includes a manifold (not shown). The manifold is similar to that included in the system 100 of FIG. 1.

The conduits 214, 224, 226 and 248 are counter-flow and comprise both feed and return flow channels configured within a single conduit. These channels can be arranged within the conduit in any of a number of configurations, such as but not limited to, the multi-lumen configurations, as shown in FIGS. 4 and 5. FIG. 4 shows a co-axial conduit 414 that comprises both a feed conduit 410 and a return conduit 412, together with the associated air flow pattern in the vicinity of the outlet. FIG. 5 shows a multi-lumen conduit 514 that comprises both a feed conduit 510 and a return conduit 512, together with the associated air flow pattern in the vicinity of the outlet. Additionally, as the feed and return channels are positioned adjacently within each conduit 414 and 514, each conduit can also comprise an interface serving as a surface for heat exchange, which thereby compliments the function of the heat exchanger that is a separate module. Other examples of multi-lumen conduits with different cross-sectional geometries are shown in FIG. 6. Any suitable multi-lumen conduit may be used, for example, having any air flow pattern that provides counter-flow. For example, the air flow pattern shown in either of FIG. 4 or 5 can be reversed to achieve the same counter-flow. The conduits can also provide measurable cooling through skin contact.

In operation, air is drawn into the system 200 through a blower similar to the blower 152 of FIG. 1 and pre-cooled by a heat exchanger similar to the heat exchanger 154 of FIG. 1. Water is vaporized into an aerosol of micron-sized droplets using an ultrasonic nebulizer similar to the ultrasonic nebulizer 156 of FIG. 1, evaporatively cooling the air. The air is then further cooled by passing over a TED cold side similar to the TED cold side 160 of FIG. 1. The cooled air is distributed to the body via the supply conduit 248, main conduits 224 and 226, and conduits 214. Further cooling of the air occurs as it passes convectively over the body of the wearer owing to the evaporation of body perspiration, creating a micro-environment within the system 200. The air is then extracted using the same conduits 214, 224, 226, and 248, but rather than discard the cooler air that has been created, this return air is passed through the heat exchanger and is used to cool the intake air and then exhausted through a blower similar to blower 153 of FIG. 1. A general configuration of the cross-over heat exchanger for both systems 100 and 200 of FIGS. 1 and 2, respectively, is shown in FIG. 3. A garment 266 is fitted over the conduits 214, 224, 226, and 248.

In an operating example of FIGS. 1 and 2, using body perspiration only, ambient air is drawn into the system 200 at 48° C. and a relative humidity of 16%. This air is passed over the body and interacts by evaporation of perspiration that effectively cools it to 41° C. with a relative humidity of 55%. This outgoing air passes through the cross-over heat exchanger that is cross connected with the intake air. The exhaust air is then used to pre-cool the intake air.

With respect to the cross-over heat exchangers described herein, any suitable regenerative heat exchanger may be used.

Any suitable power source used herein may be used to power the component(s) of the manifold.

The blower used in the above described embodiment can be any mechanical device that blows, such as, and without being limited thereto a fan, high speed centrifugal blower, oscillaters, to produce a flow of gas, such as air. The blower can be in any suitable position within the system. For example, and without being limited thereto, the blower can also be situated prior to the air entering the conduit and/or after the air exits the conduit. There can also be any number of blowers. This is applicable to the various embodiments described herein.

The conduits (e.g. tubes, ducts, channels, 3-dimensional materials, etc.) may be any suitable member conveying the flow of gas. The conduit(s) may be of any suitable size, shape, number and/or configuration capable of controlling the wearer's body temperature. The conduit(s) may have wall openings to permit further airflow. The conduit(s) may also be porous. There may be a combination thereof (e.g. porous, non-porous, wall openings etc.). The conduits may be multi-lumen or single lumen. The configuration of the channels in the multi-lumen conduits may assume any configuration, and is not limited to any specific configuration described herein, such as co-axial.

The system may be coupled to any suitable garment. For example, the system may be sewn to the garment, such as but not limited to sewing or through the use of a hook-and-loop type material such as Velcro™. The system can simply be operatively coupled to the garment, whereby the system relies on the garment to provide a flow barrier between the wearer and the outside environment to allow the body temperature of the wearer to be better controlled. The system may be connected to and operatively coupled to the garment. The system may be operable between the garment of the wearer and the wearer's skin or between layers of garments.

The system may be made of any suitable material such as, and without being limited thereto, a polymeric material. The polymeric material can be flexible to facilitate installation, removal, and movement of the wearer.

The manifold may comprise a TED and/or a nebulizer, or may comprise neither. Any suitable TED and/or nebulizer may be used. For example, while the above embodiment describes an ultrasonic nebulizer, the nebulizer may be any of, but not limited to, a rotary nebulizer, a spray nebulizer, or an ultrasonic nebulizer. Additionally, the nebulizer can be replaced with any device that provides evaporative cooling through the production of an aerosol of liquid droplets. The air entering the system can also be further cooled by passing it through an evaporator of a vapor compression refrigeration system.

The TED may be configured to be detachable to the system so as to provide operational flexibility in environments in which TED body temperature control is not required. To this end, the TED may be housed in a detachable module for convenience.

The TED and the nebulizer may each be operated independently or in conjunction with one another so as to provide body temperature control for a range of climate conditions. For example, in tropical conditions (moderate temperature, high humidity), evaporative cooling provided by the nebulizer could be thermodynamically suppressed by the high ambient humidity and could be consequently less effective, while the cooling provided by the TED could predominate. Alternatively, in "high desert" conditions (high temperature, low humidity), evaporative cooling provided by the nebulizer could be highly effective and could exceed the cooling provided by the TED. To optimize the system performance for the given conditions, and to thereby optimize power efficiency, a variable control could be provided for each of the nebulizer and the TED such that the control of active cooling could be tuned to achieve the most comfortable temperature depending on the ambient conditions.

For this purpose, and in a typical embodiment, the nebulizer and the TED may be individually and variably controlled by the wearer or automatically adjusted using a thermostat, for example. Moreover, the devices may be operated simultaneously.

The TED may be reversibly operable, whereby reversing the polarity of the power supplied to the TED could allow it to effectively operate as a heater instead of a cooler. This feature could be beneficial for use at night or in colder climates. When the system is operated in this heater mode, the nebulizer could be deactivated so as to not provide cooling.

A number of commercial TED-based devices for power generation may also be used. These systems generate power from vehicle waste heat such as exhaust and could be used to provide additional power for cooling and battery charging.

Figure 33:
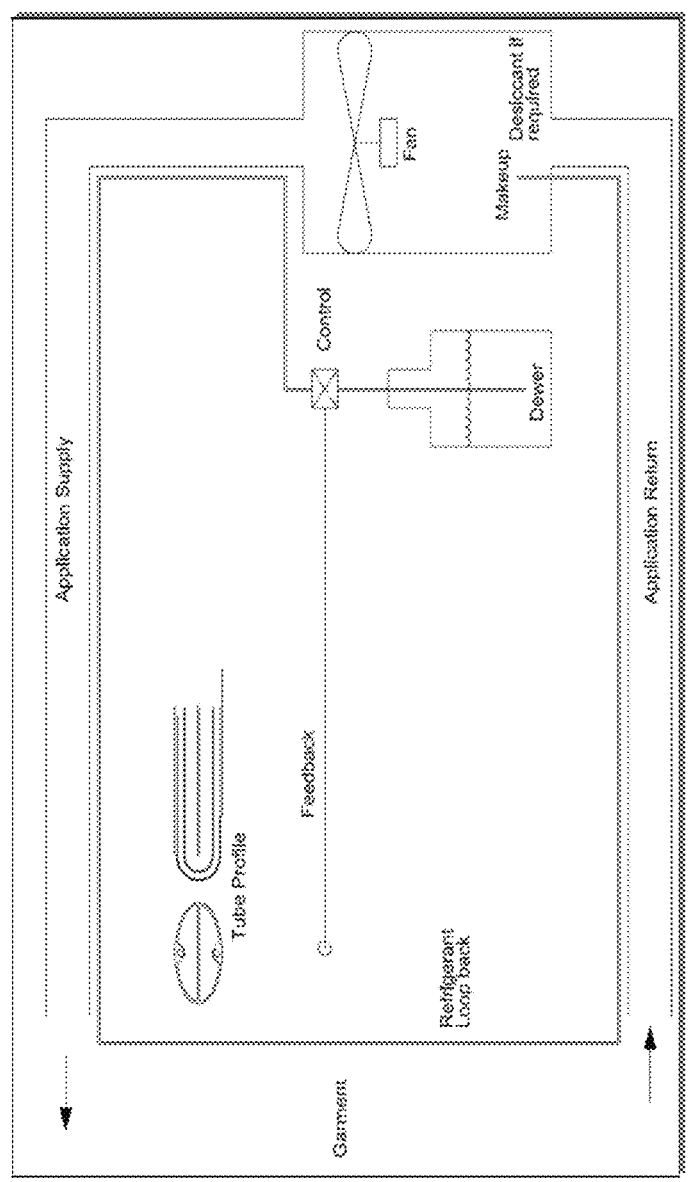
FIG. 33 shows a schematic of an embodiment of a cooling source.
Figure 34:
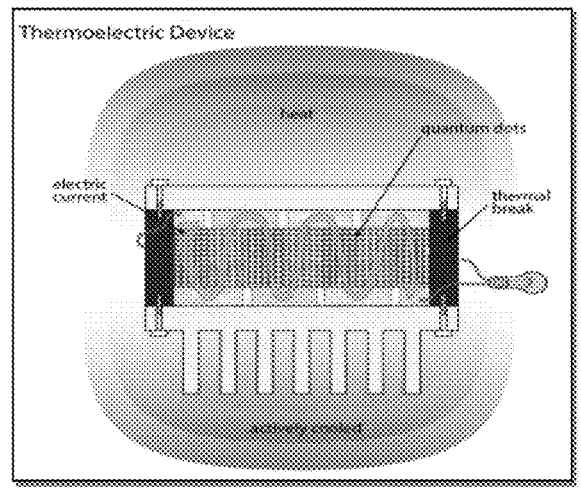
FIG. 34 shows a schematic of an embodiment of a TEG.

Besides TEDs, other cooling sources may be used. For example, cooling sources are liquid nitrogen ($LN_2$) or frozen carbon dioxide ($CO_2$ dry ice) (FIG. 33); see U.S. Pat. No. 6,751,963. In the case of $LN_2$, a water cooler sized generator is available as a commercial off the shelf system (see FIG. 34). This will require electrical power to operate a small high efficiency fan as well as the environmental controls; however, it will not require batteries. Instead it will use a solid state, thermoelectric generator (TEG) to provide power (FIG. 34). The TEG will use the temperature differential between the cooling source and the warm side air in the garment and convert it to electricity. The large temperature differential available will minimize the size of the heat sinks required and will provide instant power when the refrigerant is loaded, eliminating the need for batteries.

The manifold can be located on or near any suitable area of the body.

Any suitable gas can be used in the above-described system.

An alternative embodiment of a body temperature controlling system is shown in FIGS. 7 to 10 and indicated generally by numeral 700. The system 700 comprises conduits 714 coupled and in communication with a supply conduit 748. The conduits 714 are arranged such that the torso is suitably covered by several conduits 714. The supply conduit 748 is parallel to the spine of the wearer and extends from one end 746 (at the waist of the wearer) to the other end 747 (at the nape of the neck of the wearer). The end 747 of the supply conduit 748 is in communication with a manifold 750 that is in communication with the several battery packs 764 located around the waist of the wearer. Battery packs 764 supply power to the various components of manifold 750. In a typical embodiment, the manifold 750 comprises a blower, a cross-over regenerative heat exchanger and a nebulizer similar to those described in FIG. 1. Separate therefrom, and in communication therewith, is a TED 758 located on the shoulder of the wearer. A garment 766 is fitted over the conduits 714 and 748.

Figure 9:
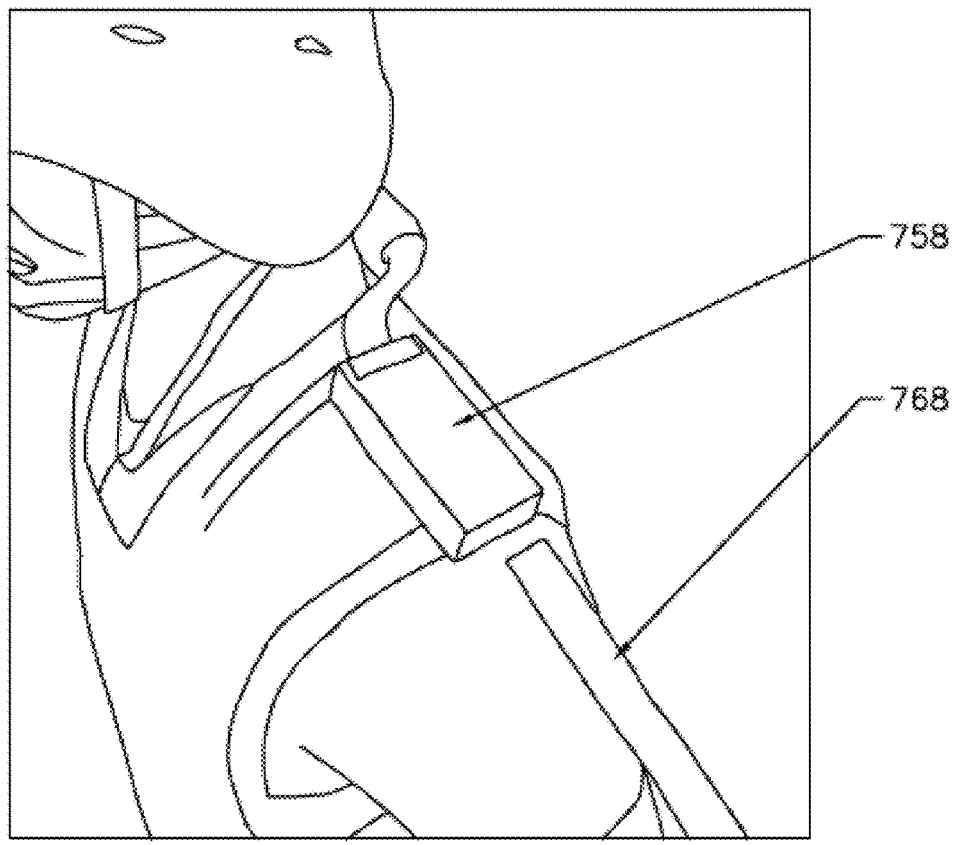
FIG. 9 shows a top perspective view of an embodiment showing one position of a TED.
Figure 10:
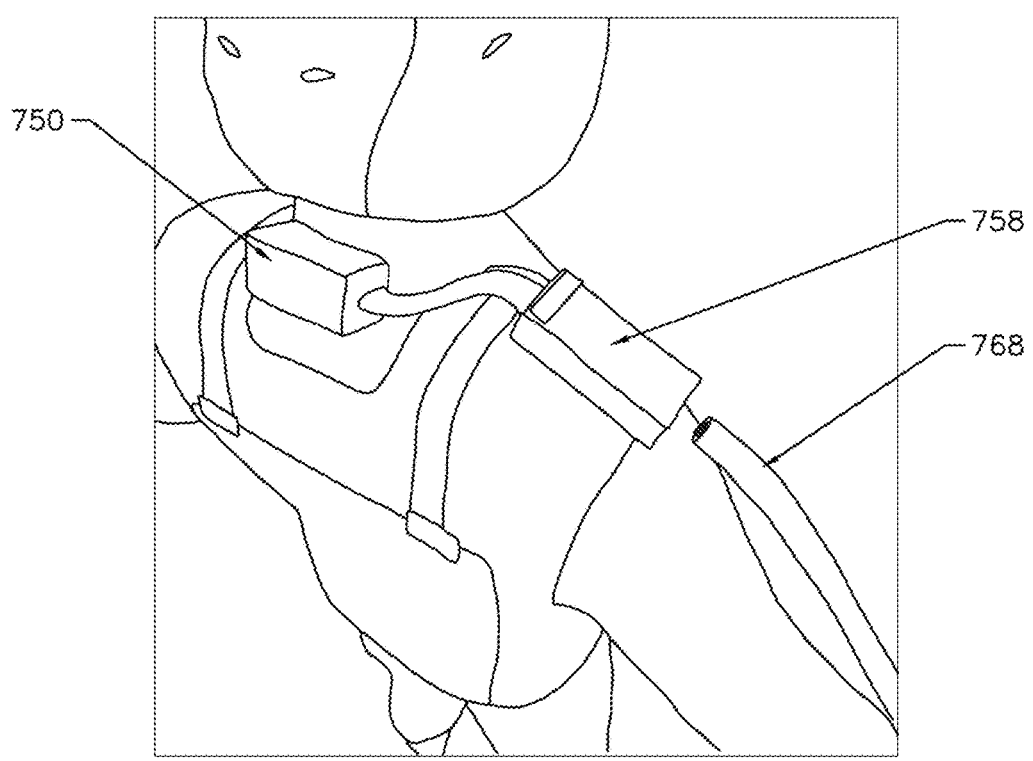
FIG. 10 shows a top perspective view of an embodiment showing another position of a TED.

The TED 758 may be configured to be readily detachable from the system so as to provide operational flexibility in environments in which TED 758 body temperature control is not required. To this end, the TED 758 may be housed in a detachable module for convenience. Other configurations and component placements are possible using this approach. This embodiment is also flexible from a mounted operations standpoint as the TED 758 can be worn on any suitable area of the body. For example, and as shown in FIGS. 9 and 10, the TED 758 can be worn on either shoulder allowing the TED 758 to exhaust out of the vehicle regardless if the user is seated in the driver or passenger side. This exhausting could be facilitated by a flex duct 768, shown in FIGS. 9 and 10, which could be configured to connect to TED 758 in a quick and simple fashion.

In operation, the system 700 operates similarly to system 200 described above, and also incorporates its operational, functional, and material embodiments. The system 700 acts to control the wearer's body temperature, for example, to maintain a comfortable body temperature for the wearer.

Figure 11:
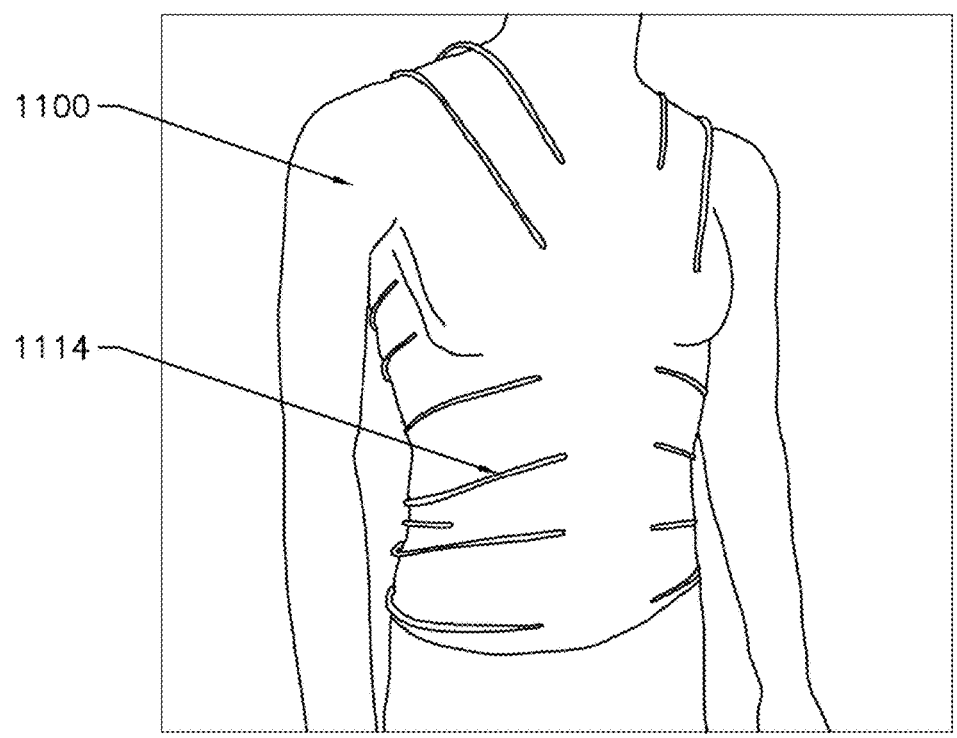
FIG. 11 is a photograph showing a front perspective view of another embodiment of a body temperature controlling system on a wearer.
Figure 12:
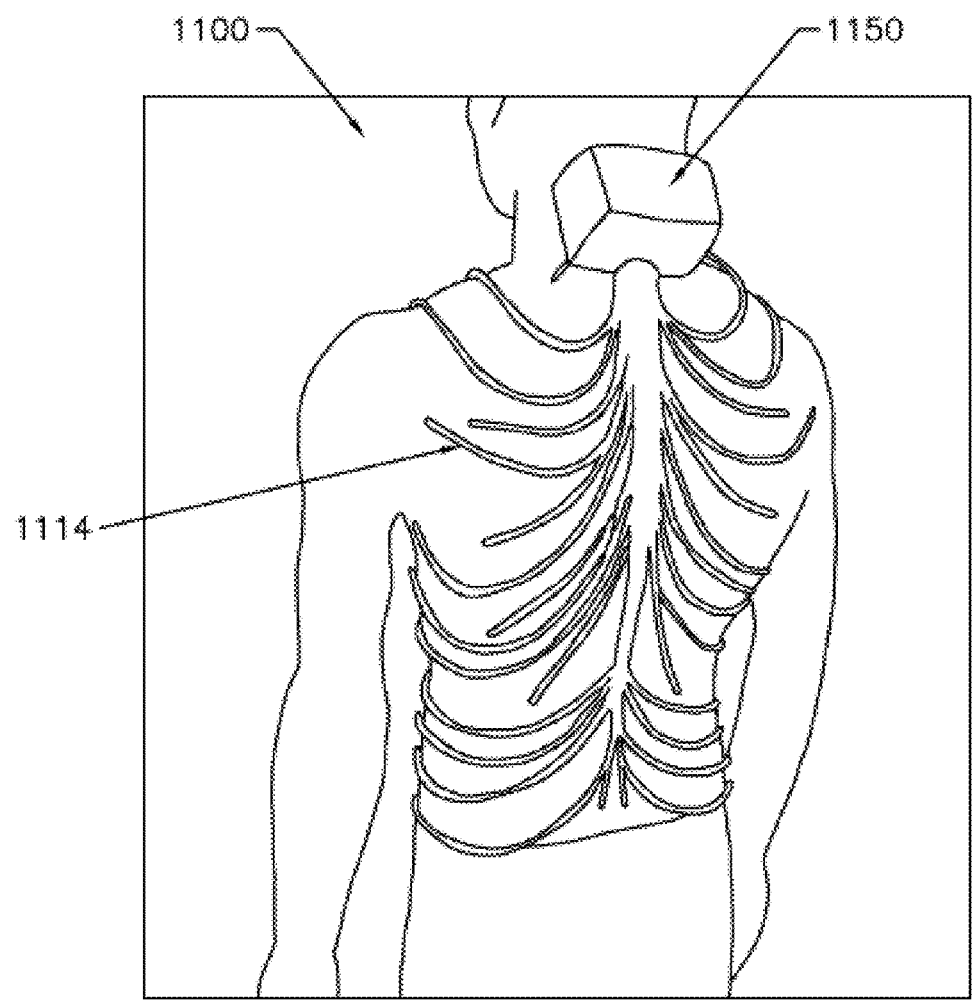
FIG. 12 is a photograph showing a rear perspective view of the body temperature controlling system of FIG. 11.
Figure 13:
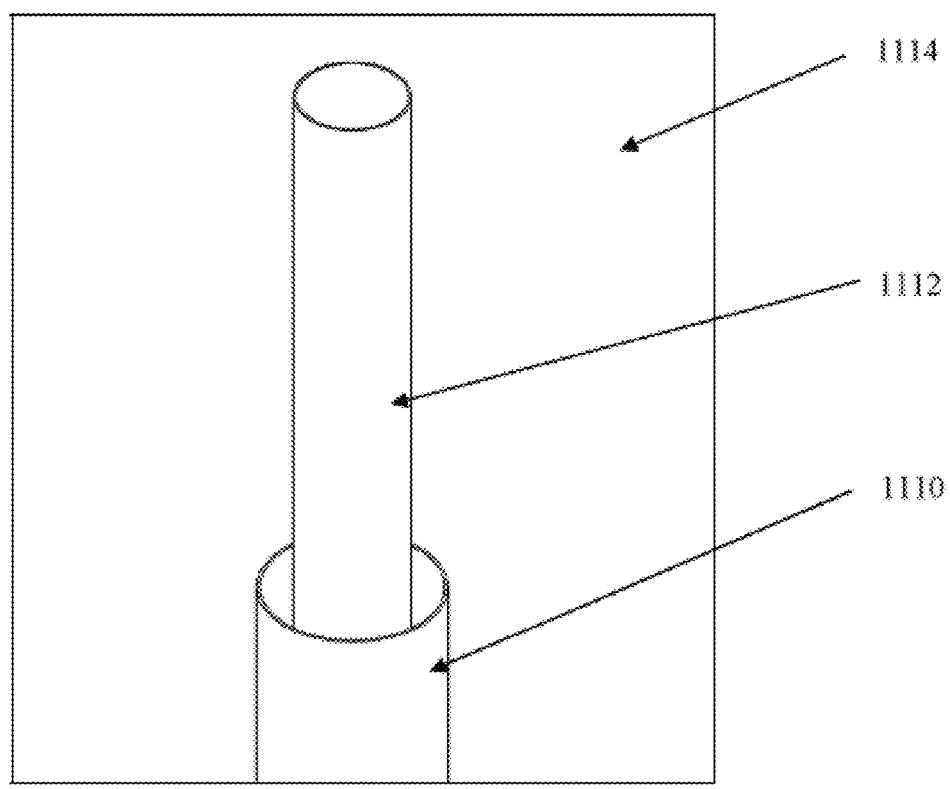
FIG. 13 shows a perspective view of the coaxial conduit of FIG. 4.
Figure 14:
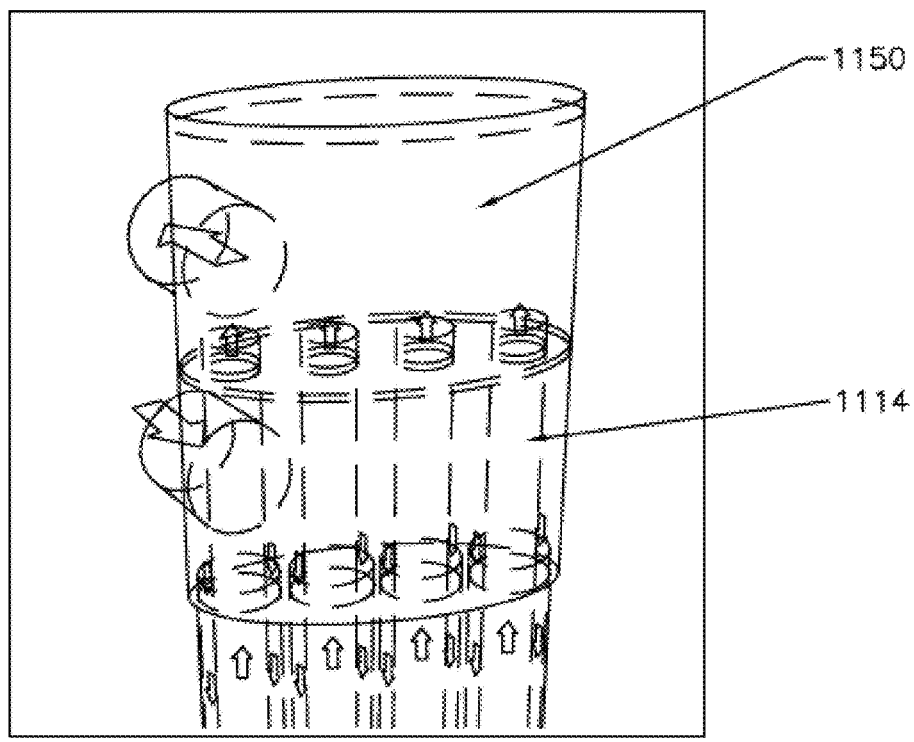
FIG. 14 shows a partial view of an embodiment of a coaxial conduit, counter flow manifold.
Figure 15:
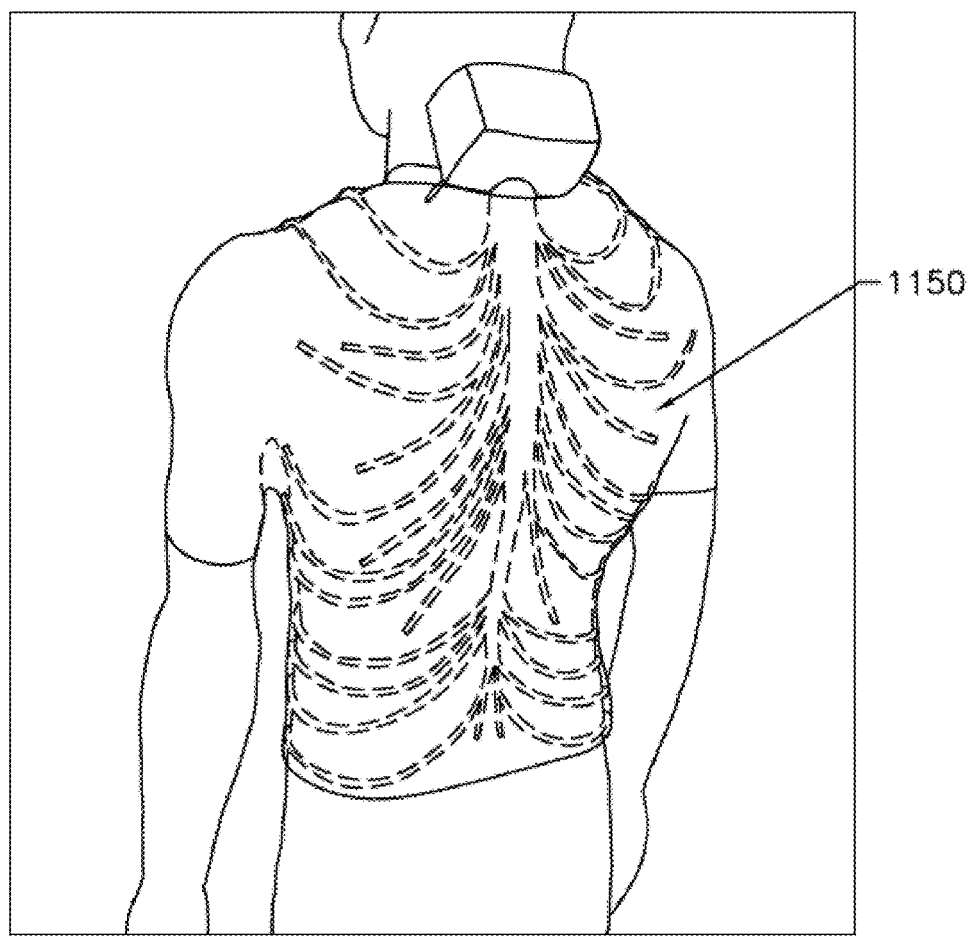
FIG. 15 is a photograph showing a rear perspective view of the body temperature controlling system of FIG. 11 under a shirt.
Figure 16:
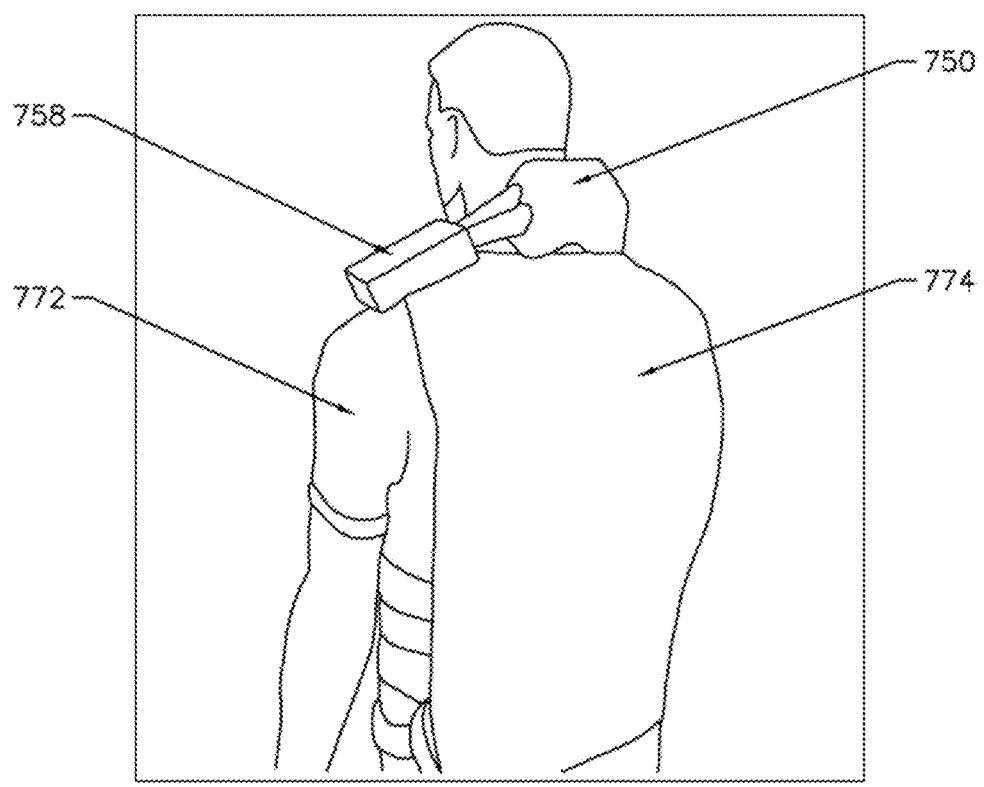
FIG. 16 is a photograph showing a rear perspective view of the body temperature controlling system of FIG. 7 under a shirt and vest.

In another embodiment, a body temperature controlling system is shown in FIGS. 11 and 12 and is indicated generally by numeral 1100. This temperature controlling garment 1100 contains several conduits 1114 of varying lengths suitably covering the back of the wearer. Some of the conduits 1114 are long enough to extend to the front of the wearer. Air distribution within system 1100 relies on the use of conduits 1114 without any main conduits or supply conduits. The conduits 1114 are coaxial microtubes as shown in FIG. 13. The feed conduit 1110 operates under positive pressure and the return conduit 1112 runs on negative pressure. This creates a pressure balance and a condition of recirculation at the application point. One end of the conduits 1114 interconnects with a manifold 1150 located at the nape of the wearer's neck. A simple model illustrating a counter-flow manifold 1150 concept for use with conduits 1114, and the associated flow paths, is shown in FIG. 14. While only four conduits 1114 are illustrated to be in communication with manifold 1150 in the example shown in FIG. 14, it is appreciated that a greater number of conduits 1114 are accommodated by manifold 1150 in FIGS. 11 and 12. FIG. 15 shows the application of a shirt 1172 over the system 1100. FIG. 16 shows the application of a shirt 772 and a vest 774 over the system 700.

The system 1100 may also include a blower, a regenerative heat exchanger, a nebulizer, a TED (similar to those described in FIG. 1) and a power source. In operation, the system 1100 operates similarly to system 200 described above, and also incorporates its operational, functional, and material embodiments. The system 1100 acts to control the wearer's body temperature, for example, to maintain a comfortable body temperature for the wearer.

In experimental testing of system 1100, thirty-six tubes were used in the embodiment shown in FIGS. 11 to 15 with an average tube length of 17 inches. The outer tube had an outer diameter of 0.144" and the inner tube had a diameter of 0.078". Both tubes had a wall thickness of 0.007". The total weight of all the tubes was less than 59 grams. Using a baseline airflow requirement of 35 cubic feet per minute, flow calculations were performed. This aspect of the design is driven in part by fan design and efficiency in order to minimize size and power requirements. The power consumption is about 25 W. The power consumption shows a fan with good efficiency and relatively low power consumption.

Figure 17:
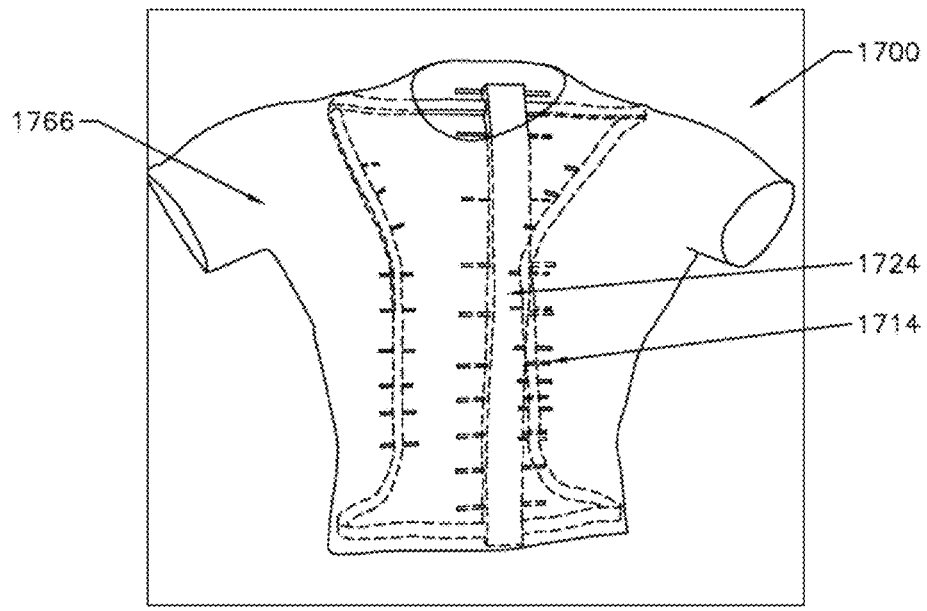
FIG. 17 shows a rear perspective view of another embodiment of a body temperature controlling system.
Figure 18:
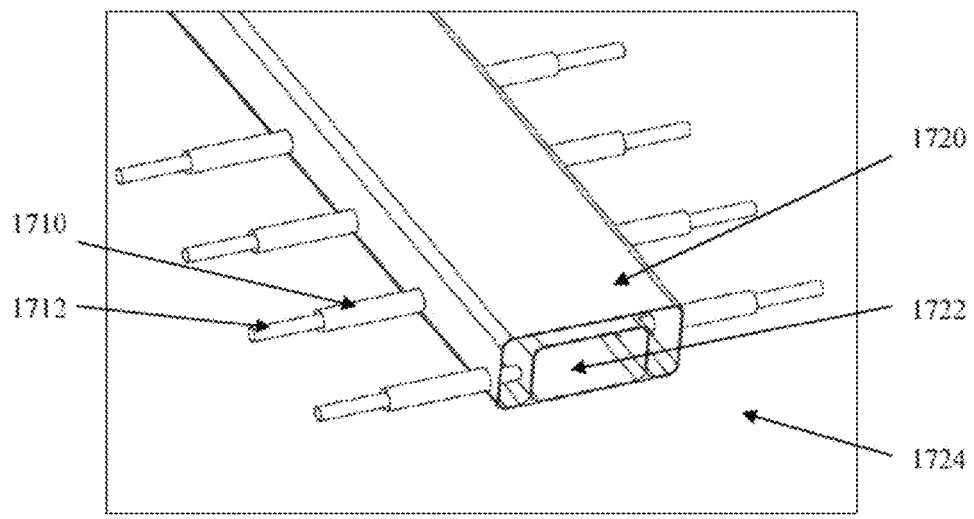
FIG. 18 shows a perspective view of conduits of the embodiment of FIG. 17.

Another embodiment of a body temperature controlling system is shown in FIGS. 17 and 18 and is indicated generally by numeral 1700. The system 1700 comprises conduits 1714 coupled and in communication with a supply conduit 1724. The conduits 1714 are co-axial tubes, each having a feed conduit 1710 and a return conduit 1712. The supply conduit 1724 has a main feed conduit 1720 and a main return conduit 1722. The feed conduit 1710 is coupled to and in communication with the main feed conduit 1720 and the return conduit 1712 is coupled to and in communication with the main return conduit 1722. The supply conduit 1724 has a generally rectangular shape and occupies a thinner profile than a cylindrical conduit of the same cross-sectional area. Such a thinner profile renders system 1700 potentially less bulky as compared to other embodiments, which can be advantageous for certain operations or applications.

The system 1700 may also include a manifold, a blower, a regenerative heat exchanger, a nebulizer, and a TED (similar to those described in FIG. 1), a power source and a garment. In operation, the system 1700 operates similarly to system 200 described above, and also incorporates its operational, functional, and material embodiments. The system 1700 acts to control the wearer's body temperature, for example, to maintain a comfortable body temperature for the wearer.

Figure 2:
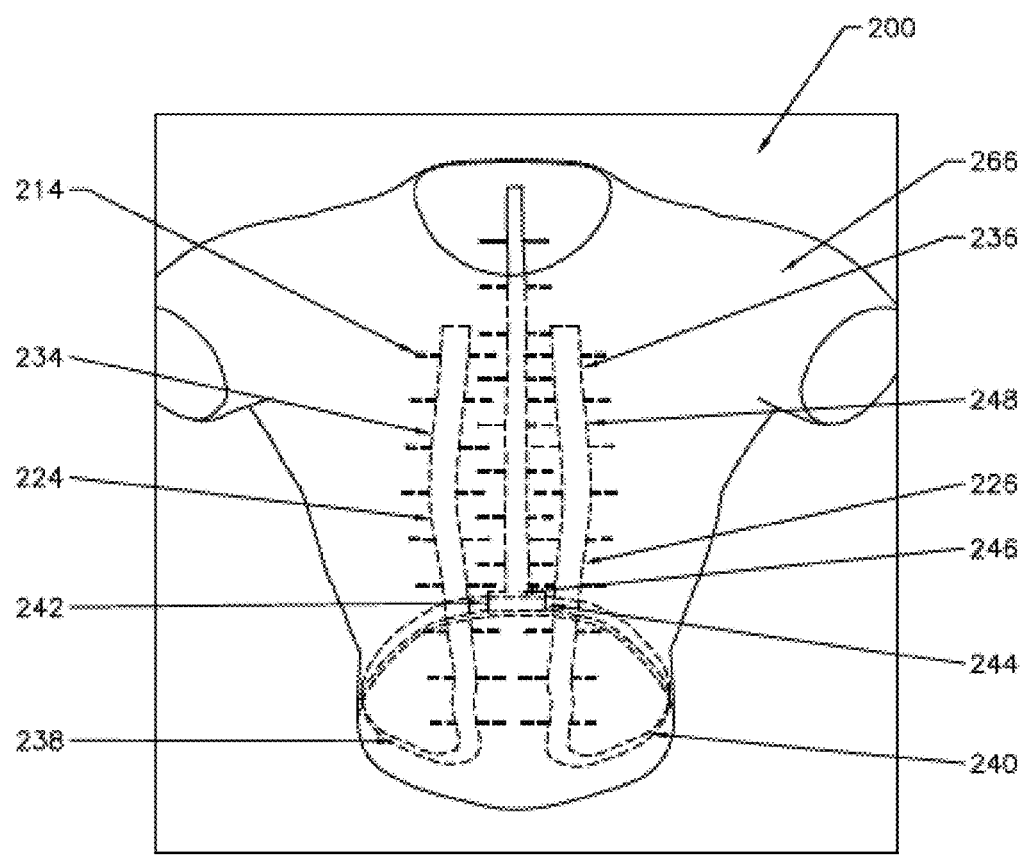
FIG. 2 shows a front perspective view of the body temperature controlling system of FIG. 1.
Figure 3:
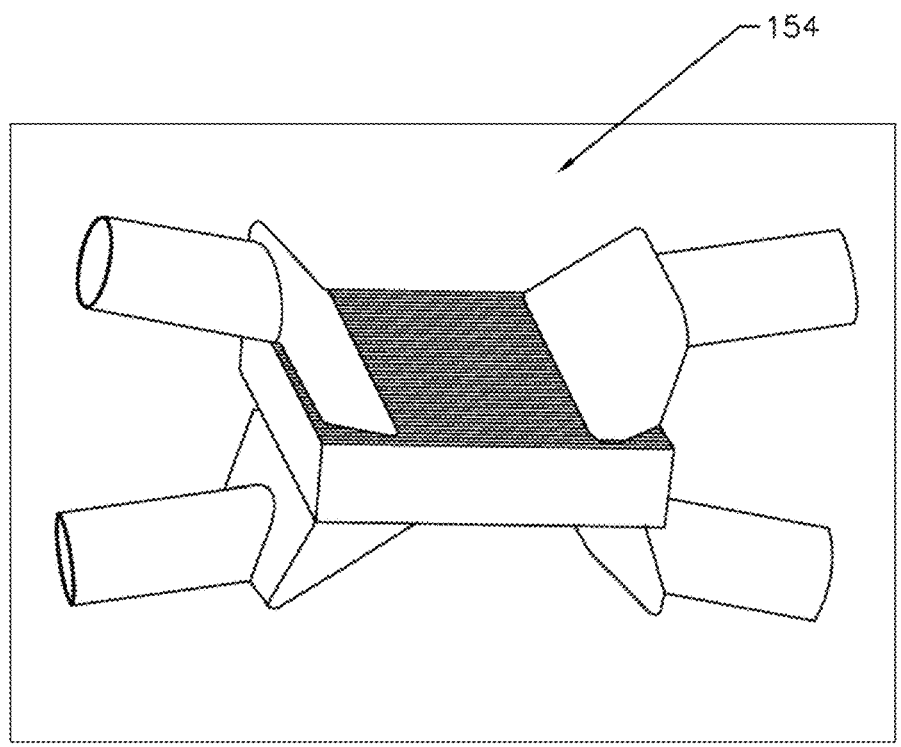
FIG. 3 shows a perspective view of one embodiment of a regenerative heat exchanger.
Figure 4:
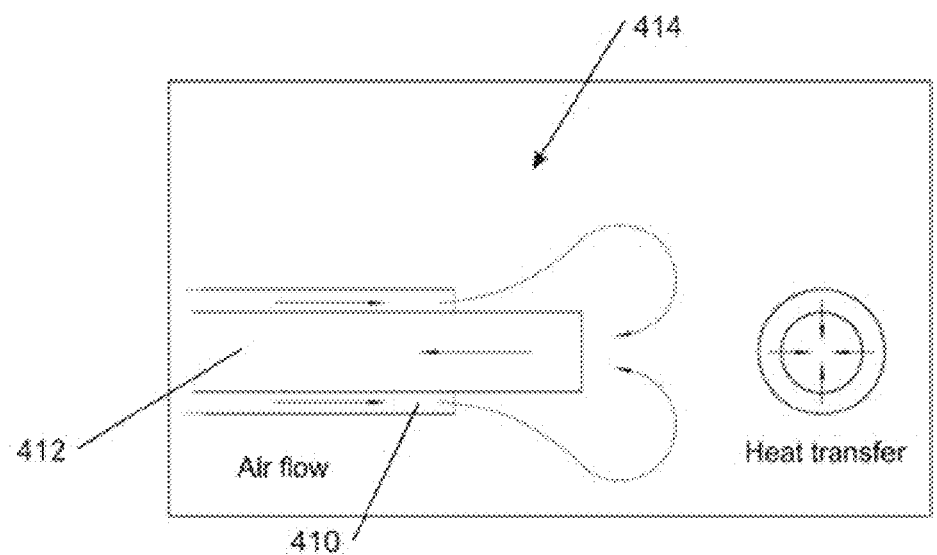
FIG. 4 shows a sectional view of one embodiment of a multi-lumen conduit, specifically, a coaxial conduit.
Figure 5:
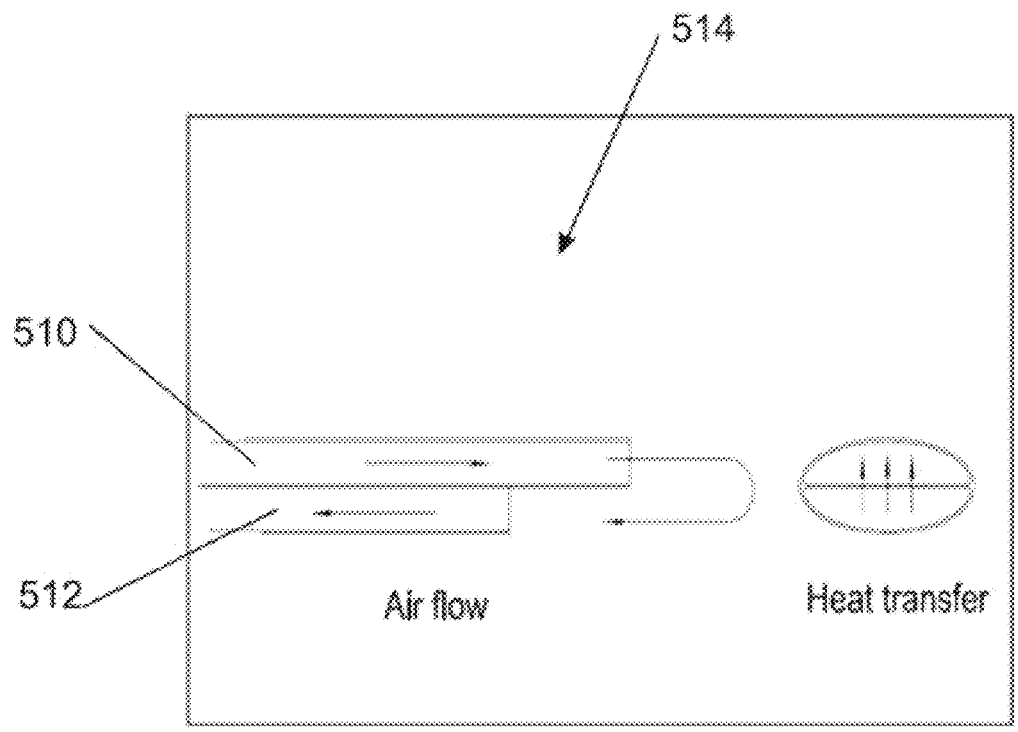
FIG. 5 shows a sectional view of one embodiment of a multi-lumen conduit.
Figure 6:
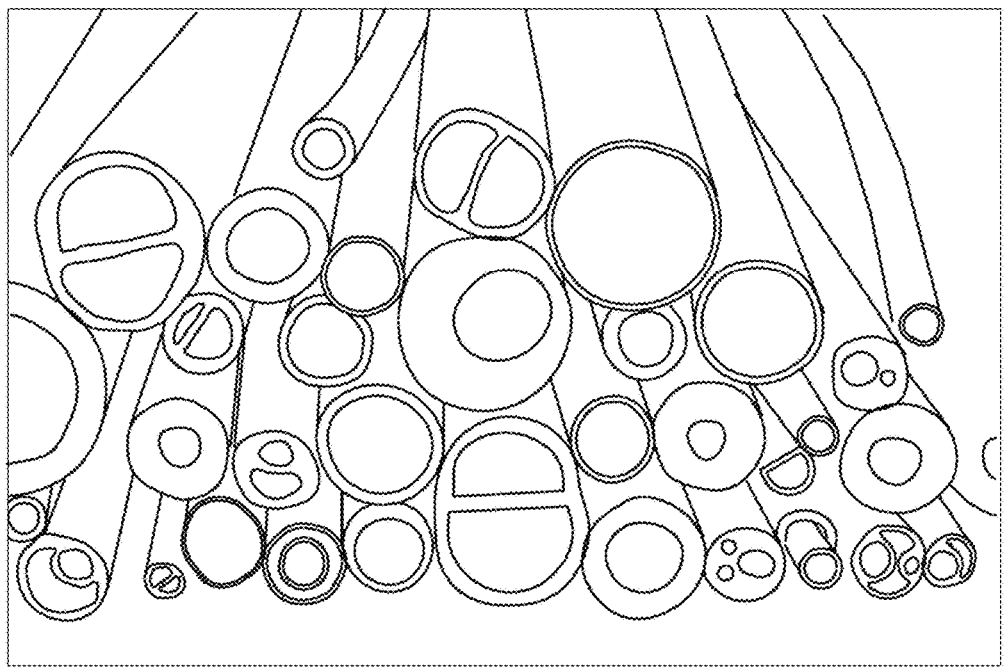
FIG. 6 shows end view of some embodiments of multi-lumen conduits.
Figure 7:
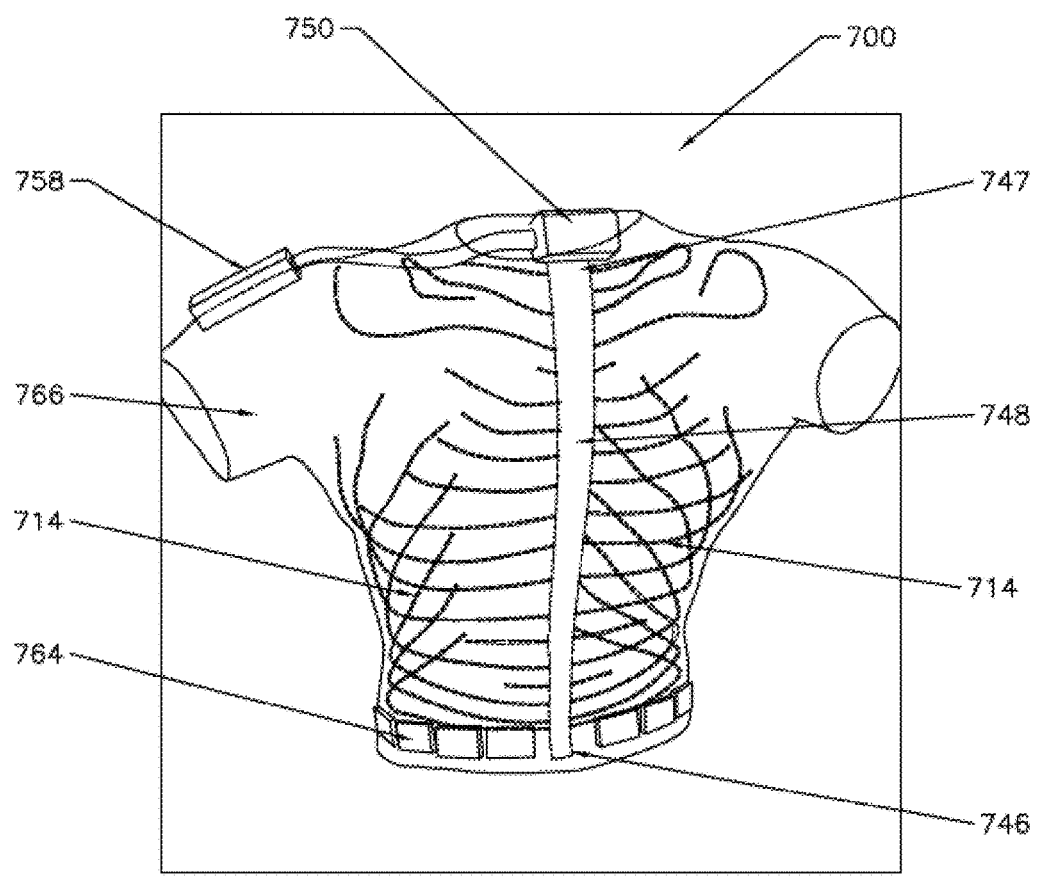
FIG. 7 shows a rear perspective view of another embodiment of a body temperature controlling system.
Figure 8:
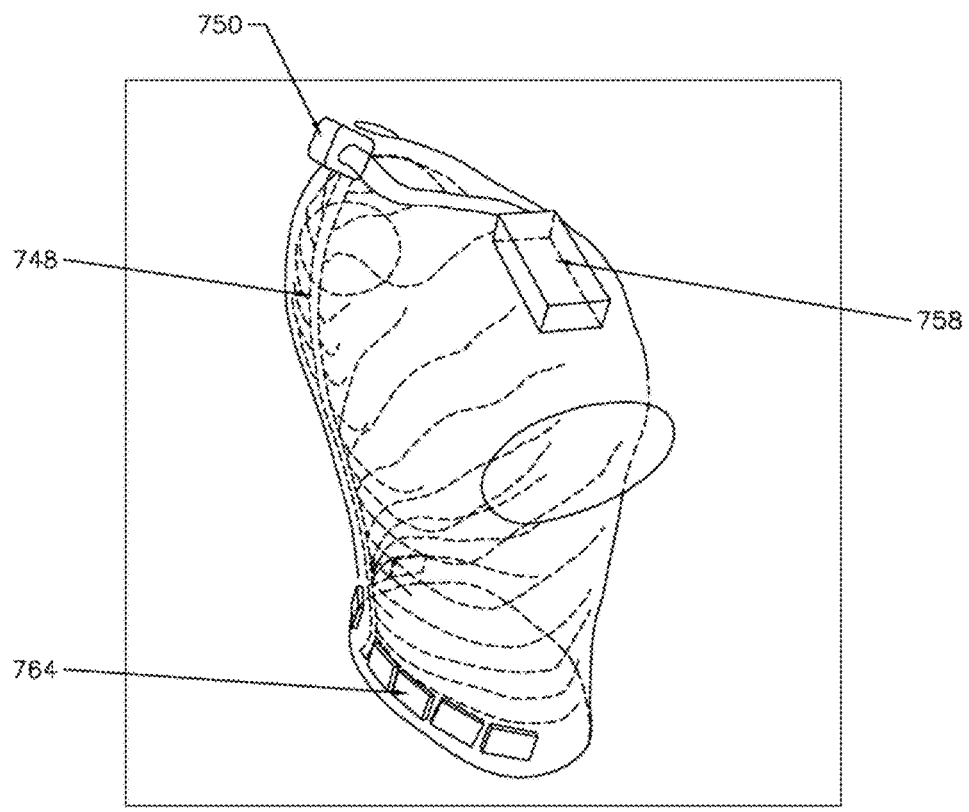
FIG. 8 shows a side perspective view of the embodiment of the body temperature controlling system of FIG. 7.
Figure 19:
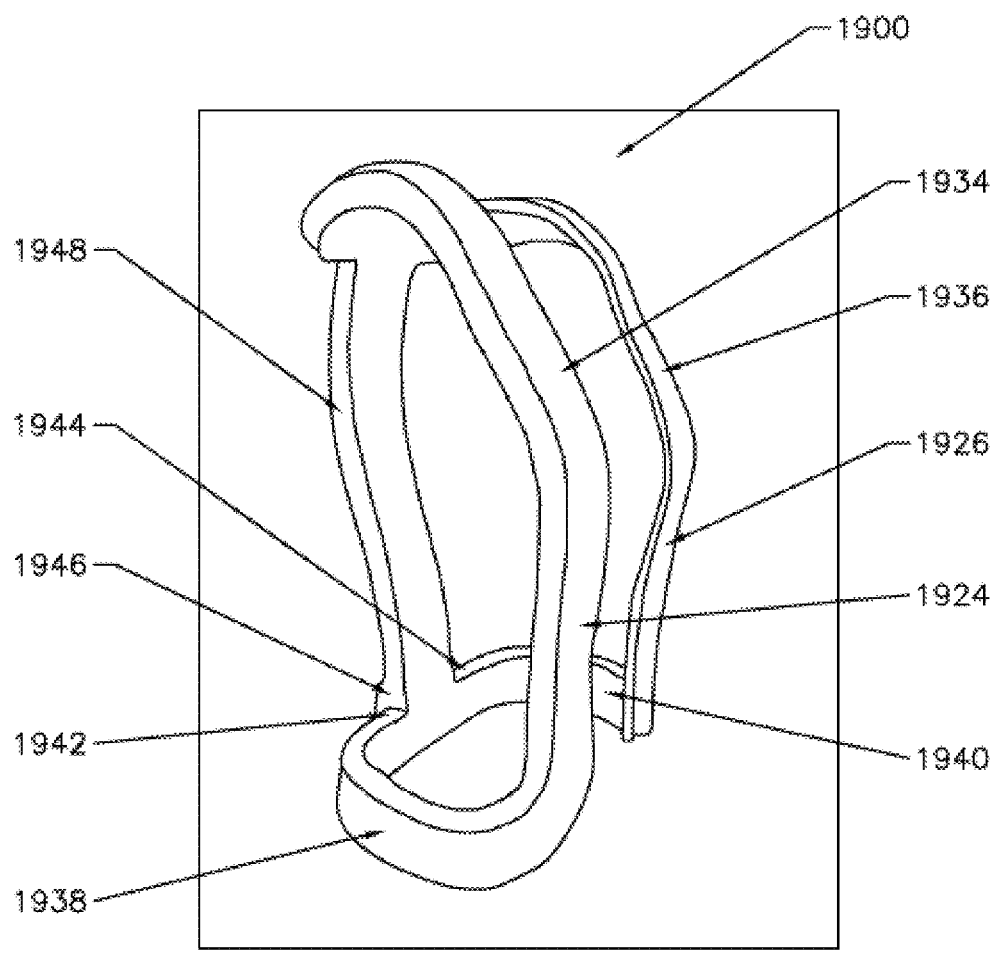
FIG. 19 is a photograph showing a side perspective view of an embodiment of a body temperature controlling system.
Figure 20:
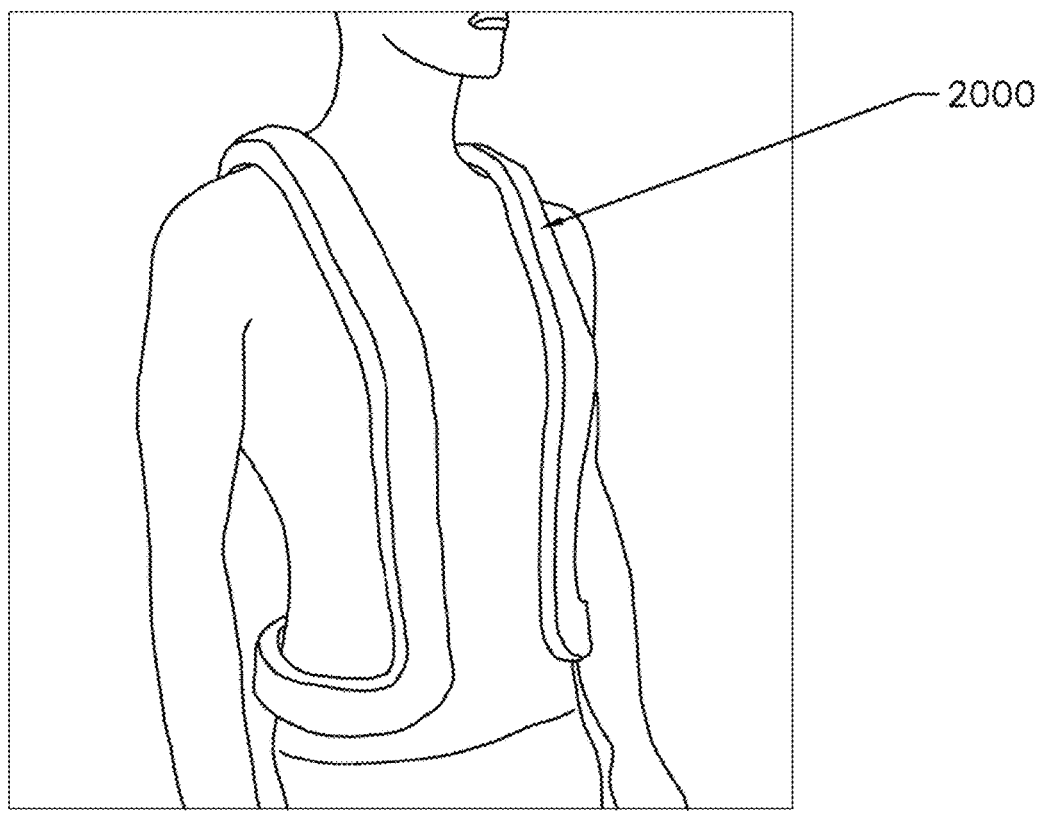
FIG. 20 is a photograph showing a front perspective view of an embodiment of a mold for formation of the body temperature controlling system of FIG. 19.
Figure 21:
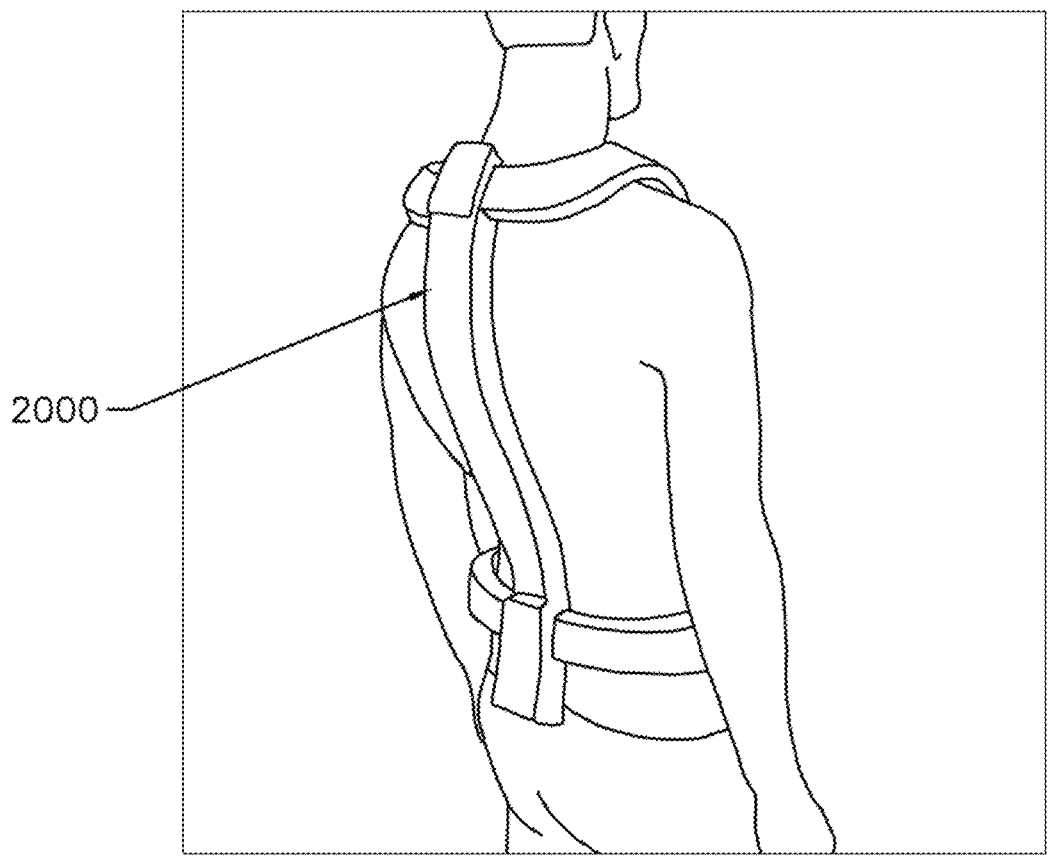
FIG. 21 is a photograph showing a rear perspective view of the embodiment of the mold of FIG. 20.
Figure 22:
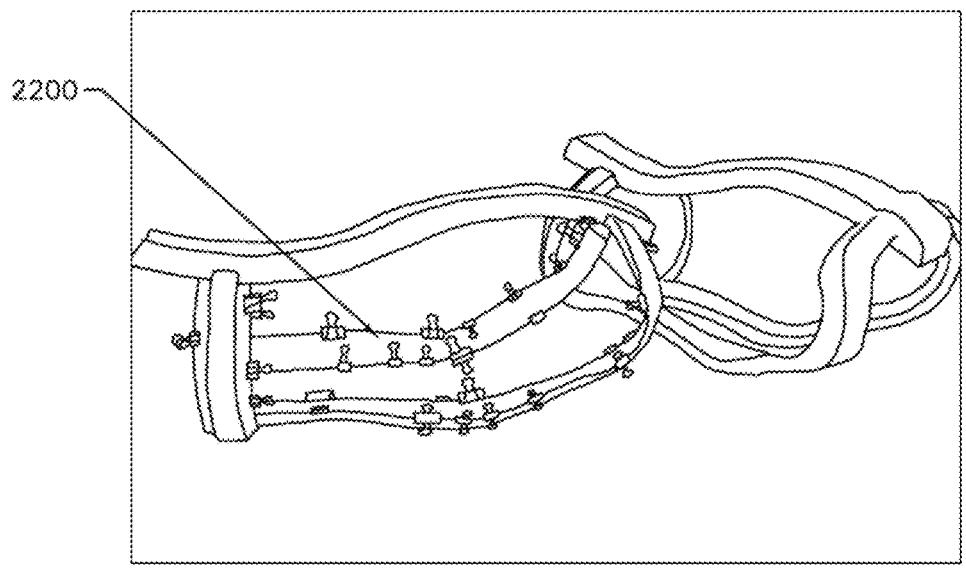
FIG. 22 is a photograph showing a side perspective view of a pre-form product molded from the mold of FIG. 20.

Another embodiment of a body temperature controlling system is shown in FIG. 19 and indicated generally by numeral 1900. The system 1900 comprises conduits (not shown but similar to the conduit 214 shown in FIG. 2) coupled and in communication with main conduits 1924 and 1926 (similar to the main conduits 224 and 226 shown in FIG. 2). The conduits (not shown) are arranged such that the torso is suitably covered with several conduits. The main conduits 1924 and 1926 are L-shaped, wherein first portions 1934 and 1936 of main conduits 1924 and 1926 are parallel to the vertical axis of the body of the wearer and are spaced apart from one another. These portions 1934 and 1936 extend over the shoulders of the wearer and are in communication with a supply conduit 1948. A second portion 1938 and 1940 of each main conduit 1924 and 1926, respectively, is perpendicular to the vertical axis of the body of the wearer, wherein one main conduit 1924 continues around the waist of one side of the wearer via second portion 1938 while the other main conduit 1926 continues around the waist of the other side of the wearer via the second portion 1940. Ends 1942 and 1944 of the main conduits 1924 and 1926, respectively, terminate at one end 1946 of a supply conduit 1948, and the main conduits 1924 and 1926 are thereby in communication with the supply conduit 1948. The supply conduit 1948 also comprises conduits 1914 (not shown) coupled and in communication therewith. The system 1900 was developed directly on a human form using a mold 2000 for formation of the body temperature controlling system of FIG. 19 (see FIGS. 20 to 22). A composite material was laid over the mold 2000 to form a pre-form product 2200 shown in FIG. 22.

The system 1900 includes a manifold (not shown). The manifold is similar to that included in the system 100 of FIG. 1. In operation, the system 1900 operates similarly to system 100 described above, and also incorporates its operational, functional, and material embodiments. The system 1900 acts to control the wearer's body temperature, for example, to maintain a comfortable body temperature for the wearer.

Figure 23:
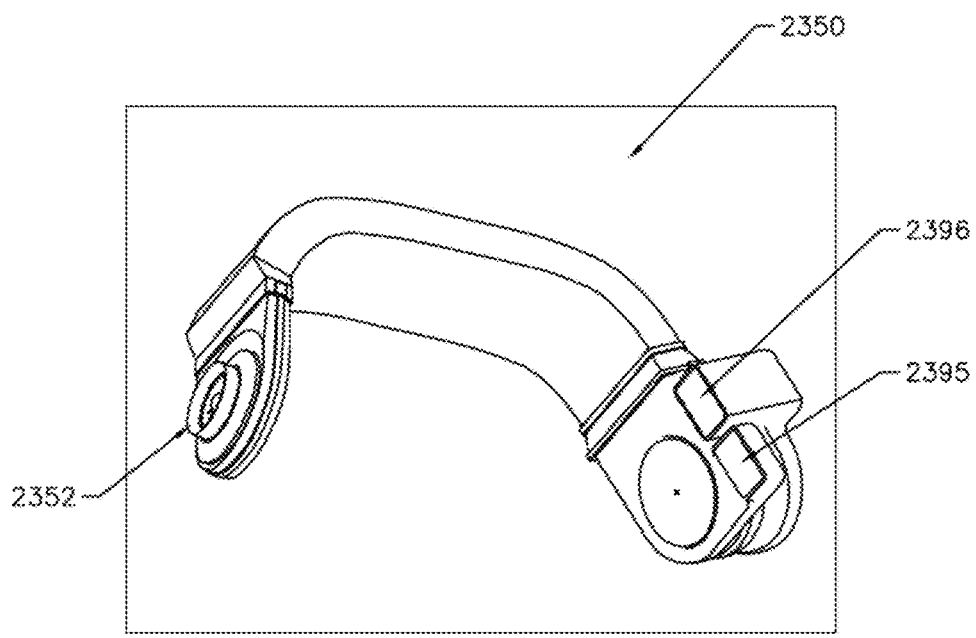
FIG. 23 shows a perspective view of an embodiment of a manifold of an embodiment of a body temperature controlling system.
Figure 24:
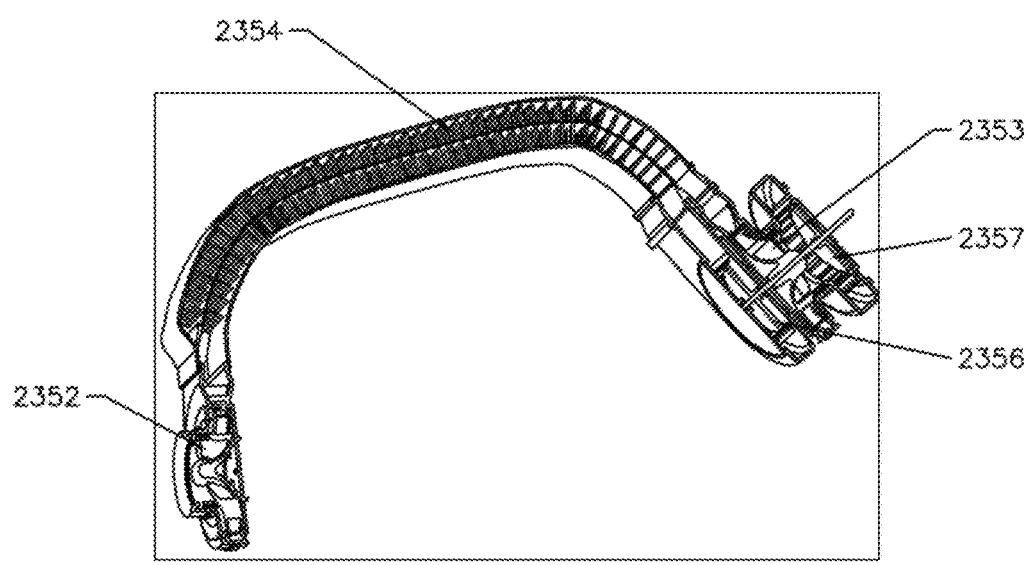
FIG. 24 shows a cross-sectional view of the manifold of FIG. 23.
Figure 25:
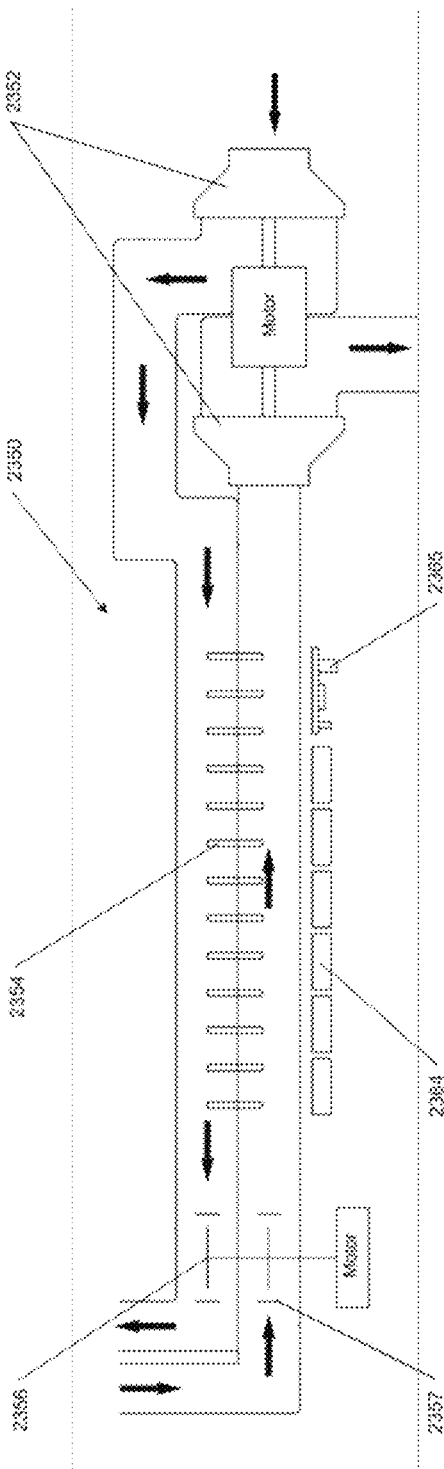
FIG. 25 shows a schematic view of the manifold of FIG. 23.

In another embodiment, a manifold of an embodiment of a body temperature controlling system is shown in FIGS. 23, 24, and 25 indicated generally by numeral 2350. The manifold 2350 is generally of a curved shape and is designed to be worn around the waist of the wearer and in communication with conduits of a body temperature controlling system which could be modified to accommodate a manifold at the waist, such as, and without being limited thereto, system 3100 of FIG. 31 described below. The manifold 2350 comprises a blower 2352 that is in communication with cross-over heat exchanger 2354. The cross-over heat exchanger 2354 is in communication with both feed nebulizer 2356 and return nebulizer 2357. The nebulizers 2356 and 2357 are positioned in the feed and return ducts of the heat exchanger 2354, respectively, and serve to cool the feed and return air respectively entering and exiting the conduits of the system described herein. The nebulizers 2356 and 2357 together form a "two-stage nebulizer", which is an efficient design whereby both rotary nebulizers are powered by a single motor, as shown schematically in FIG. 25. The manifold 2350 is in communication with feed port 2395 and return port 2396, which may interface with respective ports of the system described herein.

In operation, semi-cool return air that has been heated through exposure to the torso of the wearer can be cooled by the return nebulizer 2357 without the requirement for an additional motor or the use of additional battery power. The cooled return air, which was already cooler than the ambient, is then passed through the heat exchanger 2354 to cool the feed air prior to it passing through the feed nebulizer 2356. Also shown in FIG. 25 are battery pack 2364 and control electronics 2365. The battery pack 2364 provides power to the various components of the manifold 2350.

Figure 26:
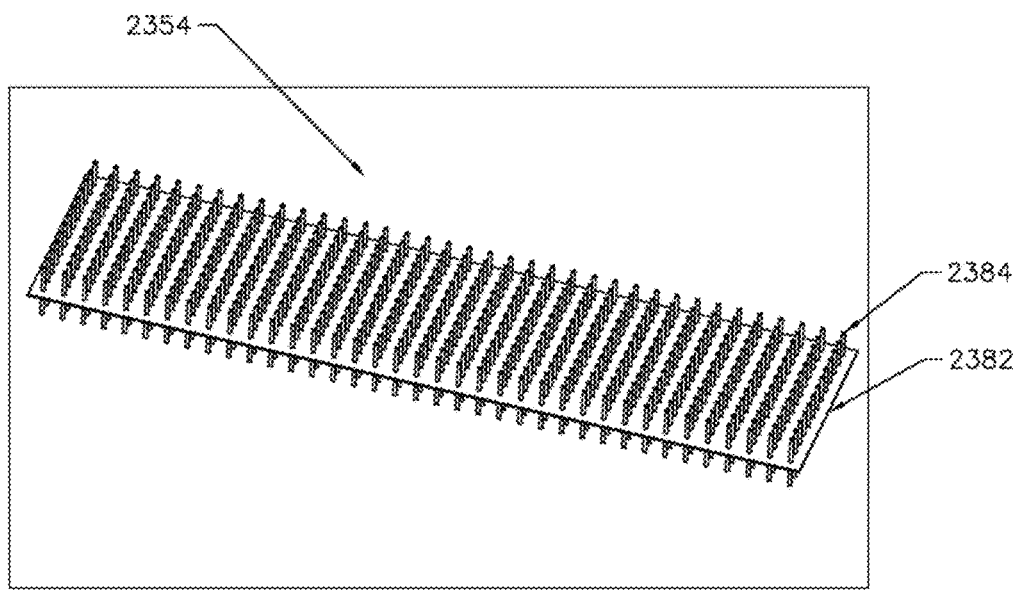
FIG. 26 is a photograph showing a perspective view of a heat exchanger of the manifold of FIG. 23.

FIG. 26 shows the heat exchanger 2354 in greater detail. The heat exchanger 2354 comprises a septum 2382 through which a plurality of pins 2384 are inserted to perforate the septum 2382. The septum 2382 is made from a flexible material to enable the manifold 2350 to flex in order to accommodate a range of waist sizes for different wearers, or to respond to the motions of the wearer. Each of the pins 2384 is inserted through the septum 2382 such that one portion of each pin extends from each side of the septum 2382 so as to provide maximum conductance of heat from one side of the septum 2382 to the other.

As mentioned above, the manifold 2350 is designed to be worn around the waist of the wearer and in communication with conduits of a body temperature controlling system, such as, and without being limited thereto, the system 3100.

The septum 2382 can be made from any suitable material. For example, metals or polymers.

The pins 2384 can be any thermally conductive members. The member(s) do not have to be inserted through the septum. The members may be applied in any configuration or manner to provide thermal conductivity. The members could be applied to one side of the septum and the other side of the septum and could be in communication with one another. This may be done via welding or brazing, for example.

Figure 27:
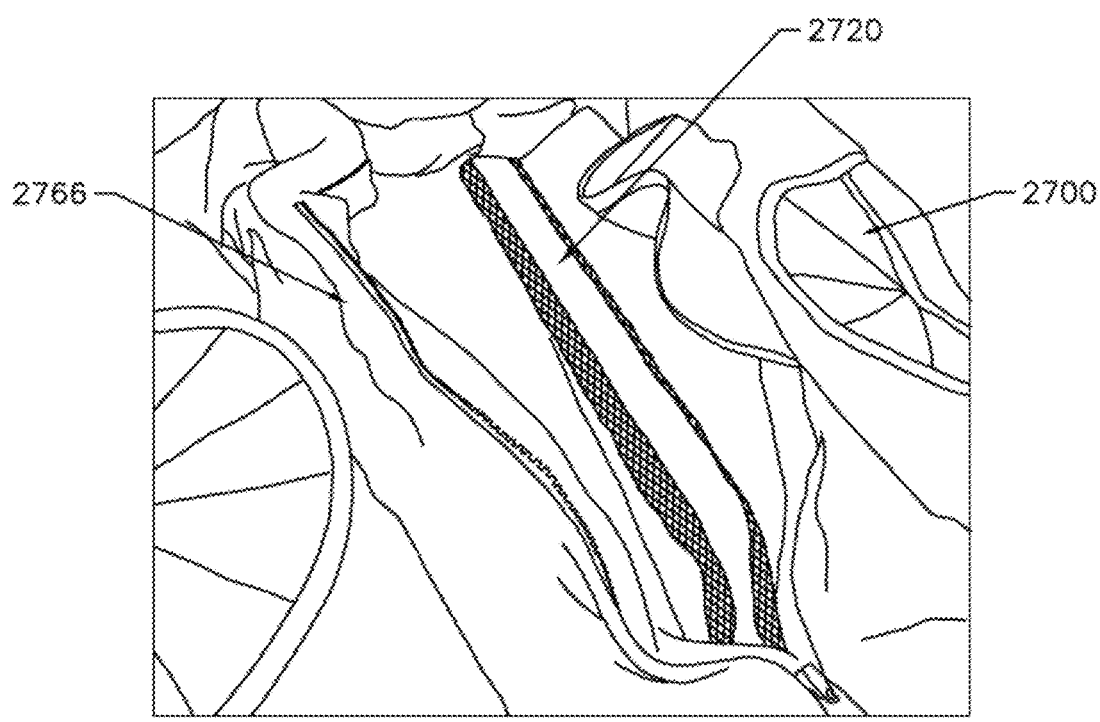
FIG. 27 is a photograph showing a perspective view of a conduit and a garment of another embodiment of a body temperature controlling system.
Figure 28:
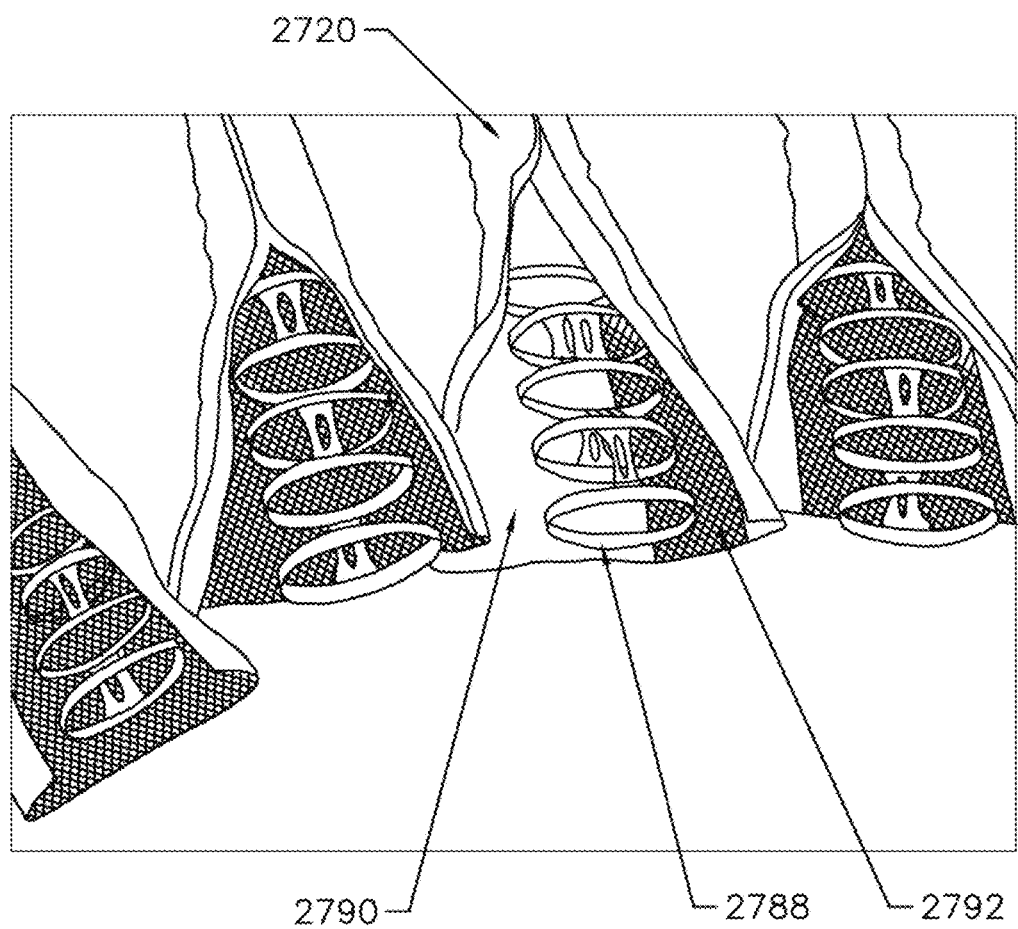
FIG. 28 is a photograph showing a perspective view of examples of the conduit of the system of FIG. 27.
Figure 29:
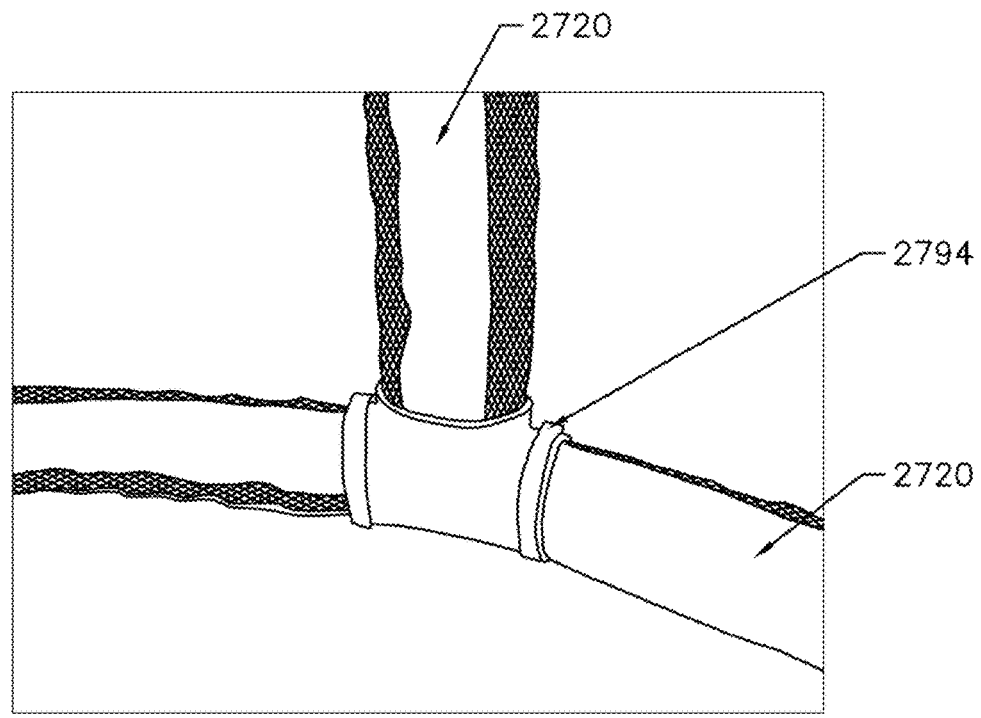
FIG. 29 is a photograph showing a perspective view of a plurality of connected conduits of the system of FIG. 27.

Still another embodiment of a body temperature controlling system is shown in FIGS. 27 to 29 and is indicated generally by numeral 2700. The system 2700 comprises one or more main conduits 2720 that are fitted within a garment 2766. The conduits 2720 each comprise a tubular frame 2788 having a skeletal structure, which is sheathed in a fabric covering 2790. The fabric covering 2790 comprises a longitudinal strip of mesh-like fabric 2792. The tubular frame 2788 is made of a polymeric material, and has an open structure that is generally both longitudinally flexible and is radially rigid, and permits gas flow both longitudinally along the longitudinal axis of the tube and through the mesh-like fabric 2792. A plurality of the conduits 2720 are brought into communication with each other using a T-connector 2794 so as to form a flexible but resilient frame of the conduits 2720 within a garment 2766. The conduits 2720 may be used in communication with a manifold comprising a blower, and may also be in communication with a nebulizer, a thermoelectric device (for example, as described in the system 100 of FIG. 1), and/or a power source.

The tubular frame may be made of any suitable flexible material.

The fabric covering 2790 may be made of any suitable fabric or sheet-like material. Various materials such as, and without being limited thereto: Banox FR3 is a 100% flame-retardant treated 100% cotton fabric; NOMEX® is a flame retardant meta-aramid material marketed and first discovered by Du Pont in the 1970s and it can be considered an aromatic "nylon"; Westex INDURA®; Westex's INDURA® Ultra Soft flame resistant fabrics; Hoechst Celanese PBI Gold; Springs Industries FIREWEAR®; KERMEL® fiber is a polyamide-imide fiber which is classified in the meta-aramide family; CarbonX® fire resistant material; and SSM Industries Pro-Fil FR® may be used. Mesh materials may be used.

The longitudinal strip of mesh-like fabric 2792 may be any suitable mesh-like fabric, which may or may not be incorporated. If the mesh-like fabric is incorporated it may be integral with or may be any portion of the fabric covering 2790.

With respect to the T-connector 2794, any suitable connectors may be used. The conduits may be integral and therefore, eliminating the connector altogether.

Figure 30:
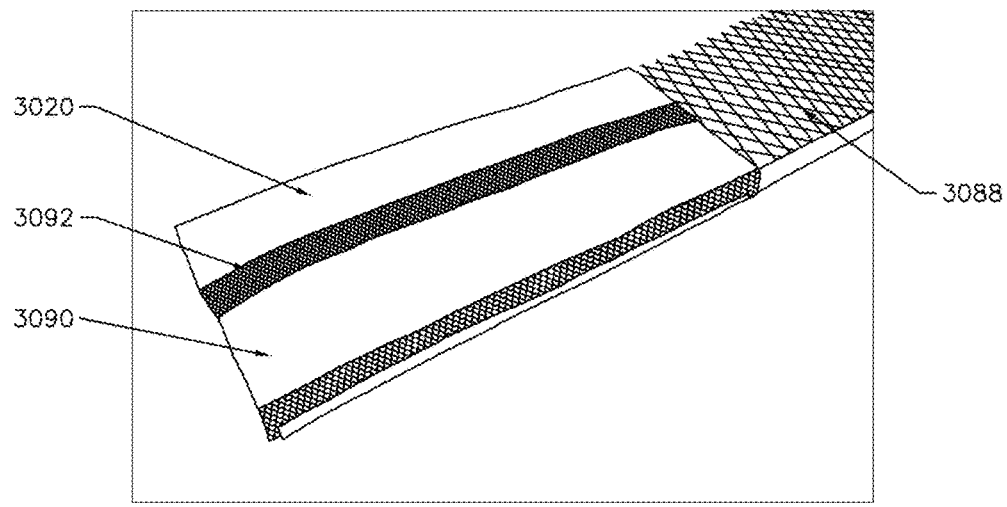
FIG. 30 is a photograph showing a perspective view of a conduit of another embodiment of a body temperature controlling system.

In a similar embodiment shown in FIG. 30, a main conduit has a generally rectangular cross section and is generally indicated by numeral 3020. The conduit 3020 comprises an internal frame 3088 comprised of a 3-dimensional mesh-like material having a generally flexible structure, which is sheathed in a fabric covering 3090. The fabric covering 3090 comprises a longitudinal strip of mesh-like fabric 3092. The internal frame 3088 is made of a polymeric material, and has an open structure that is generally both longitudinally flexible and laterally rigid, and permits gas flow both longitudinally along the longitudinal axis of the tube and transversely through the mesh-like fabric 3092. Similar variations are applicable as described above with respect to the system 2700 of FIGS. 27 to 29.

The internal frame 3088 may be any suitable 3-dimensional porous material. The internal frame may also serve as a stand-off material, wherein the internal frame is largely hollow to reduce air resistance.

Porous material or porous described herein is any material through which gas can flow.

Figure 31:
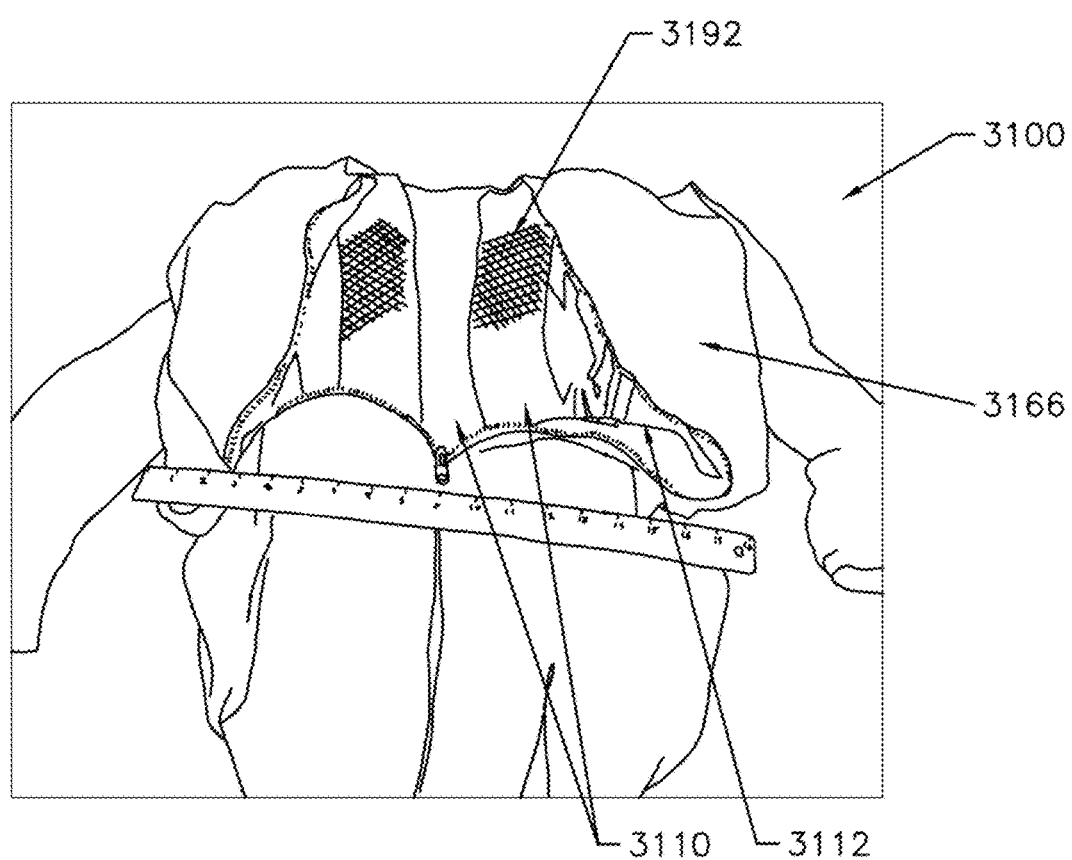
FIG. 31 is a photograph showing a perspective view of conduits and a garment of another embodiment of a body temperature controlling system.
Figure 32:
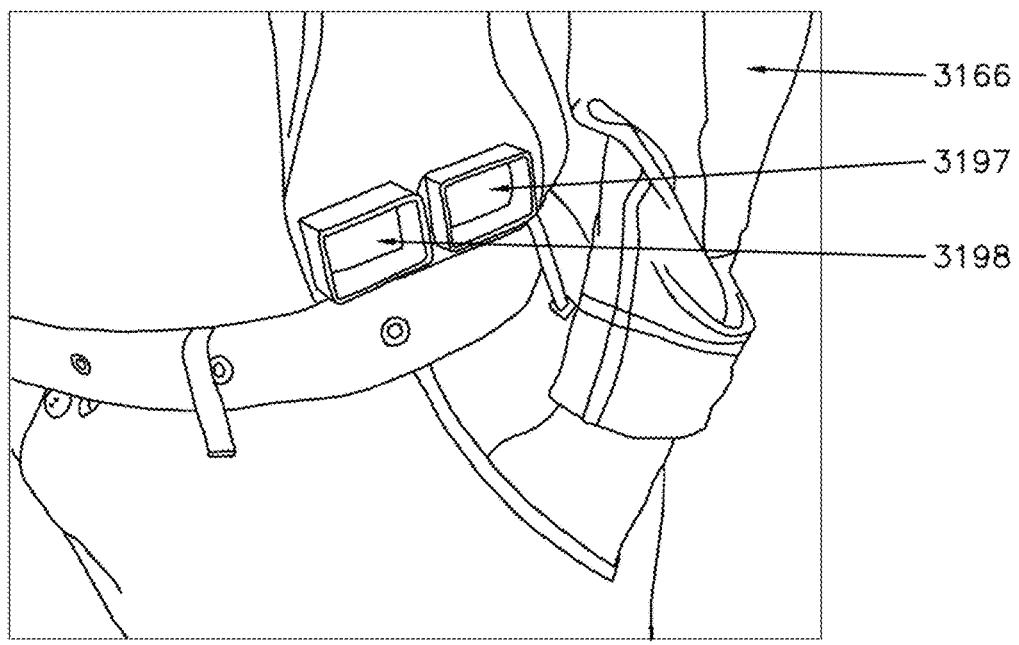
FIG. 32 is a photograph showing a perspective view of ports of the body temperature controlling system of FIG. 31.

Another embodiment of a body temperature controlling system is shown in FIGS. 31 and 32 and is indicated generally by numeral 3100. The system 3100 comprises one or more panel-shaped feed conduits 3110 and panel-shaped return conduits 3112, that are fitted within a garment 3166. The conduits 3110 and 3112 comprise an internal frame comprised of a 3-dimensional mesh-like material having a generally flexible structure, similar to the internal frame 3088 of FIG. 30, which are sheathed in a mesh-like fabric 3192. The internal frame is made of a polymeric material, and has an open structure that is generally both longitudinally flexible and laterally rigid, and permits gas flow both longitudinally along the longitudinal axis of the tube and transversely through the mesh covering 3192. A plurality of the conduits 3110 or 3112 can be brought into communication with each other using a connector (not shown) so as to form a flexible but resilient frame of the conduits 3110 and 3112 within the garment 3166. The feed conduits 3110 may be in communication with a main feed conduit (not shown), which is positioned along the waist and in the lumbar region of the wearer, and the return conduits 3112 may be in communication with a main return conduit (not shown), which is positioned along the waist and in the belly region of the wearer. The main feed conduit and the main return conduit may be in communication with a manifold comprising a blower, a nebulizer, a thermoelectric device (for example, as described in the system 100 of FIG. 1), and/or a power source. FIG. 32 shows feed port 3197 and return port 3198 that interface with the respective ports on a manifold such as, for example, the manifold 2350 shown in FIG. 23, which has matching ports 2395 and 2396, respectively, which in turn can be in communication with the conduits 3110, 3112, and the main conduits. Similar variations are applicable as described above with respect to the system 2700 of FIGS. 27 to 29 and the conduit 3020 of FIG. 30.

In operation, air is cooled in a manifold used with system 3100, and the cooled air is pumped into feed port 3197 from the manifold. The cooled air flows into the main feed conduit that is positioned parallel to the waist and in the lumbar region of the garment 3166. Feed conduits 3110 are in communication with the main feed conduit, and cooled air flows thereby from the main feed conduit to feed conduits 3110 and then over the body of a wearer of the system 3100. Air is then drawn into return conduits 3112, which are in communication with the main return conduit that is positioned parallel to the waist of the wearer and in the belly region of the garment 3166. The return air is drawn out of the main return conduit via the return port 3198 and into the manifold used with system 3100.

While the above embodiment describes the feed and return conduits as being positioned generally in the back and front of the wearer, respectively, it may be appreciated any location may be used for these conduits. While the above embodiment describes the main feed and main return conduits as being positioned generally in the lumbar and belly regions of the wearer, respectively, it may be appreciated any location may be used for these main conduits.

The panel-shaped conduits 3110 and 3112 can be any suitable shape, size or configuration to convey gas flow. For example, the conduit(s) can be any suitable width so as to occupy any portion of the garment.

With regard to the embodiments described by systems 100, 700, 1100, 1700, 1900, 2700, and 3100 the alternatives described herebefore and hereafter apply.

A controller can be used to control fan air flow and refrigerant delivery by environmental feed back within the garment. The ability to program the cooling conditions will help acclimatize the subject during initial use and conditioning. A demand controlled based system could vary the amount of airflow, water and if required TED cooling based on environmental and physiological requirements such as body temperature or temperature and humidity changes from inlet to outlet air. This could increase the efficiency and duration of the cooling system by optimizing power and water use. The system can also include a data logger to record various aspects of the system as well as the user's response.

The design of the garment of the system will depend somewhat on the activity as well as the delivered cooling and coverage area required. The garment may be any item of clothing such as a vest, shirt, pants, etc. With respect to the coverage area, for example, a garment with short sleeves and legs will provide approximately 50% coverage of the total body area, whereas a long sleeve leg version could provide >75% coverage and improve cooling. Both designs (see for example FIG. 35) could utilize a common cooling module and could be used alternatively depending on the activity, ambient conditions and level of acclimatization.

Any suitable garment material may be used. With respect to soldiers in the battle field, thermal effects from enemy ordinance such as IED's is a concern and secondary burn trauma caused by melting synthetic materials is well known. Various garment materials such as, and without being limited thereto: driFire®, Banox FR3 is a 100% flame-retardant treated 100% cotton fabric; NOME® is a flame retardant meta-aramid material marketed and first discovered by Du Pont in the 1970s and it can be considered an aromatic "nylon"; Westex INDURA®; Westex's INDURA® Ultra Soft flame resistant fabrics; Hoechst Celanese PBI Gold; Springs Industries FIREWEAR®; KERMEL® fiber is a polyamide-imide fiber which is classified in the meta-aramide family; Carbon) fire resistant material; and SSM Industries Pro-Fil FR® may be used. Mesh materials may be used.

Any standard power sources may be used with the systems of the present invention. For example, commercial and military qualified lithium ion cells are well characterized and are readily available from a number of manufacturers. As mentioned previously, typical power densities for rechargeable systems are in the range of 140~150 W·h/kg. Lithium Sulfur batteries are currently being produced with densities exceeding 300 W·h/kg and are expected to reach as high as 600 W·h/kg in the forseeable future. The lithium sulfur cell shown at the top of FIG. 40 has a nominal capacity of 2200 milliamps and weighs 15 grams. Typically, the battery pack does not transfer heat to the user or inlet air during charging or discharging. Battery packs with internal temperature sensing are available. Miniature fuel cells that are currently being developed are reported to have power densities exceeding 800 W·h/kg. These power supplies have the potential to further increase the mobility and duration of the garment and electronics cooling systems. The latest generation of field transportable electrolysers that use compact photon exchange membrane technology could be used for field generation of hydrogen as well as hydride regeneration.

The garment can be used for controlling the temperature on any area of the body (e.g. torso, head, legs, etc.).

Any suitable gas can be used in the above-described system.

As mentioned earlier, the system may also be used for warming a wearer as well.

EXAMPLE

The embodiments of FIGS. 19 to 22 are used.

A total of 74 supply micro-tubes with an average length of 3" were installed on conduits 1920, 1922 and 1938. The tubes had a nominal diameter of 0.144" and a wall thickness of 0.007". An equal number of 0.125" extractor ports were installed between the supply conduit directly on the coaxial, counter flow duct. Twenty additional 0.125" supply ports were installed under the supply and extractor conduits to provide airflow between the duct and the wearer.

Figure 35:
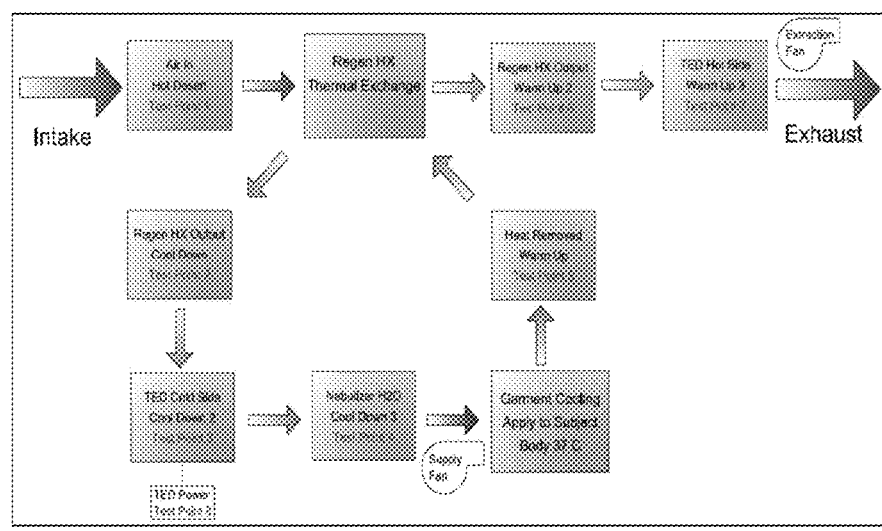
FIG. 35 shows a flow chart of system test points of an embodiment of a body temperature controlling system.

A total of seven Vaisala HPM-50, combination temperature and humidity sensors were installed in the system test points as shown in FIG. 35. In addition, a Hall Effect current detector was installed to measure TED power demand. Volumetric flow rates of the complete system including the garment were measured using an anemometer at the garment supply and extraction connection points. Static pressures were also measured at these locations.

Figure 36:
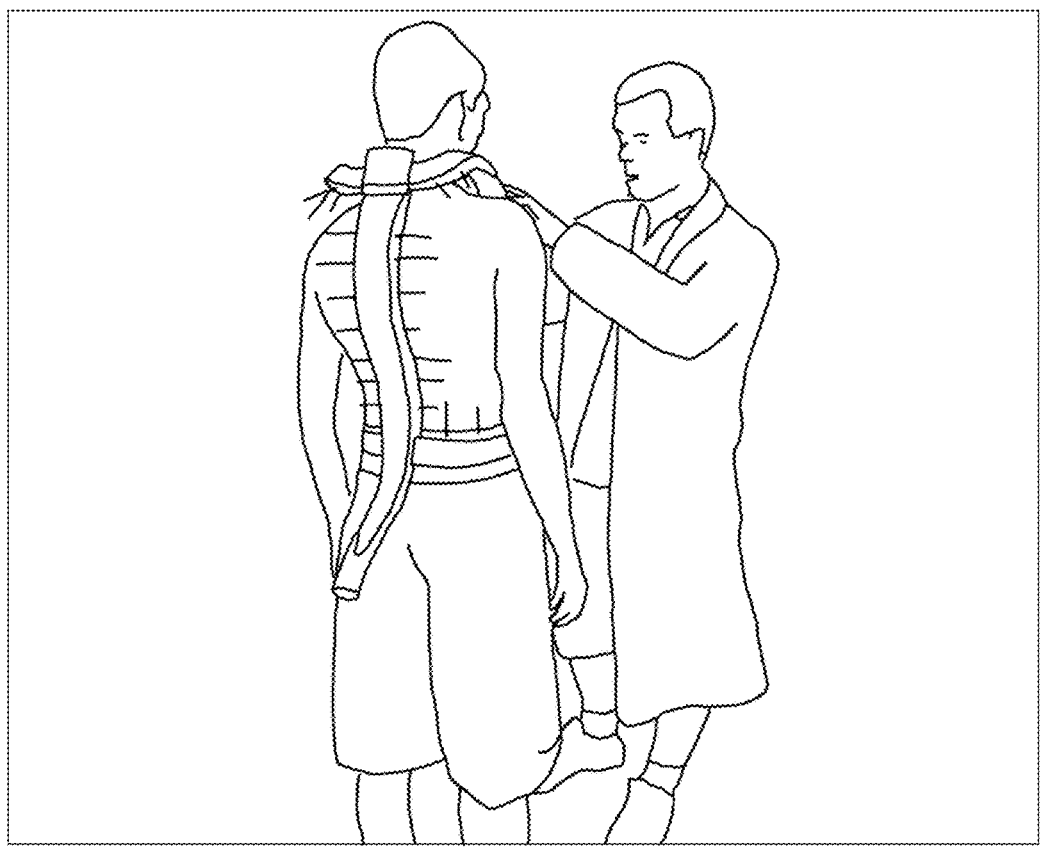
FIG. 36 is a photograph showing a perspective view of the embodiment of the body temperature controlling system of FIG. 17 on a wearer.
Figure 37:
FIG. 37 is a photograph showing a perspective view of the embodiment of the body temperature controlling system of FIG. 17 on a wearer with a vest.

The duct and outer garment were placed on the wearer with eight additional 0.144" supply and extractor conduits routed to the wearer's under garments for additional application coverage (FIG. 36). A prototype garment fabricated from Carbon-X was placed over the application system to contain the micro-environment. The camouflaged garment shown in FIG. 37 is not part of the system and was used to visualize a ballistic vest. The male test wearer was approximately 6 feet tall, 168 pounds and in good physical condition. A simple environmental chamber was prepared and conditioned to approximately 46° C. and a relative humidity of 16% using electric heating sources and dehumidifiers.

The wearer and garment were connected to the system ancillaries using flexible air hoses. The garment system fans were turned on and conditions were allowed to stabilize. Data was recorded using three system operation modes. These were regenerative only, regenerative and evaporative and finally regenerative, evaporative and TED combined.

Figure 38:
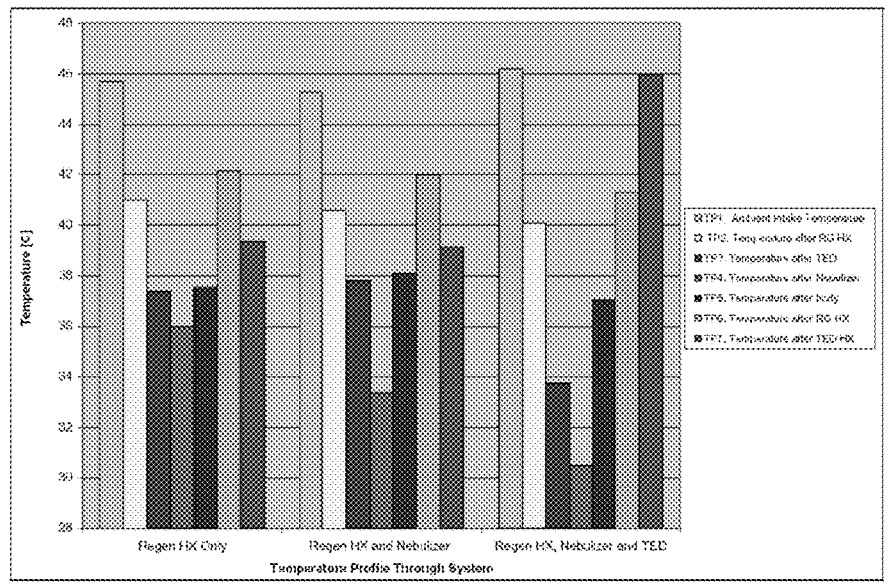
FIG. 38 shows temperature profiles for the body temperature controlling system of FIG. 17 on a wearer.
Figure 39:
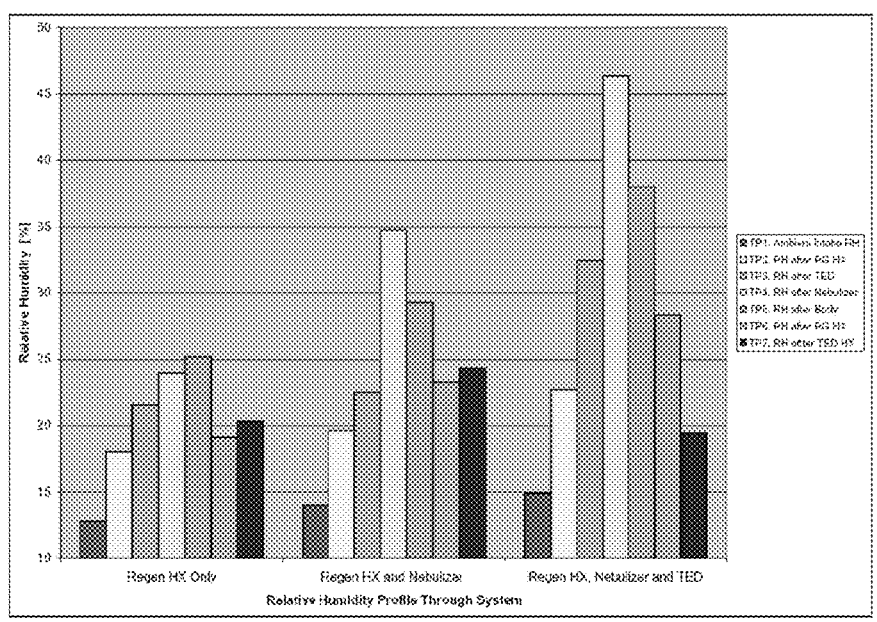
FIG. 39 shows relative humidity profiles for the body temperature controlling system of FIG. 17 on a wearer.

FIGS. 38 and 39 show temperature and relative humidity profiles through the system during the three modes of operation. The supply and extracted airflow rates during the test were 16 and 15 cubic feet per minute, respectively. Delivery pressure was 1.95 in.$H_2O$ and the return pressure was −1.55 in.$H_2O$. The nebulizer delivered approximately 1 gram of water per minute to the system during evaporate and evaporate/TED modes of operation. The wearer reported heat relief almost immediately after the system was turned on in the initial regenerative mode and was comfortable for the duration of the test.

The test wearer was sedentary during the experiment and only small amounts of water atomization and airflow were required to maintain his comfort level.

When introducing elements disclosed herein, the articles "a", "an", "the", and "said" are intended to mean that there are one or more of the elements. The terms "comprising", "having", "including" are intended to be open-ended and mean that there may be additional elements other than the listed elements.

With respect to the terms "coupled" or "coupling", these terms are understood to encompass integral with or connected thereto.

The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

What is claimed is:

1. A body temperature controlling system comprising:
   at least one member receiving a flow of gas from a manifold in communication with said at least one member, said at least one member directing said flow of gas onto a wearer thereof; and
   at least one wearable thermo-electric device in communication with the manifold, said flow of gas passing over at least one of a cold side and a hot side of said at least one wearable thermo-electric device, the manifold comprising:
   at least one blower and at least one heat exchanger, said at least one heat exchanger comprising a cross-over heat exchanger configured to cool said flow of gas using a return flow of gas previously passed over said cold side of said at least one wearable thermo-electric device and previously directed onto the wearer,
   wherein said body temperature controlling system is wearable.

2. The system of claim 1, wherein said at least one member is of a suitable size, shape, and/or configuration capable of controlling the wearer's body temperature.

3. The system of claim 1, wherein said at least one member is porous.

4. The system of claim 1, wherein said at least one member comprises a frame.

5. The system of claim 4, wherein the frame is covered with a porous material.

6. The system of claim 5, wherein the porous material is a fabric.

7. The system of claim 6, wherein the fabric comprises a mesh-like fabric.

8. The system of claim 4, wherein the frame comprises a 3-dimensional porous material having a generally flexible structure.

9. The system of claim 8, wherein the 3-dimensional porous material comprises a 3-dimensional mesh-like material.

10. The system of claim 8, wherein said at least one member is at least one conduit.

11. The system of claim 4, wherein the frame comprises a stand-off material.

12. The system of claim 1, wherein said at least one, member is at least one conduit.

13. The system of claim 12, wherein said at least one conduit comprises a plurality of conduits, said plurality of conduits having at least one feed conduit and at least one return conduit.

14. The system of claim 13 further comprising at least one main feed conduit in communication with said at least one feed conduit and at least one main return conduit in communication with said at least one return conduit.

15. The system of claim 12, wherein said at least one conduit is a counter-flow conduit.

16. The system of claim 12, wherein said at least one conduit comprises at least one multilumen conduit.

17. The system of claim 16, wherein said at least one multilumen conduit comprises at least one feed conduit and at least one return conduit.

18. The system of claim 17, wherein each said at least one multilumen conduit comprises one of said at least one feed conduit and one of said at least one return conduit, said one of said at least one feed conduit and said one of said at least one return conduit being co-axial.

19. The system of claim 17 further comprising at least one main feed conduit in communication with said at least one feed conduit and at least one main return conduit in communication with said at least one return conduit.

20. The system of claim 12, wherein said at least one conduit is at least one of a panel-shaped conduit, tube, duct, channel, and 3-dimensional porous material.

21. The system of claim 20, wherein the panel-shaped conduit comprises a suitable width so as to occupy any portion of the system.

22. The system of claim 12, wherein at least one of said at least one conduit comprises a wall having any of porosity, openings, and vents.

23. The system of claim 12, wherein said at least one conduit comprises a plurality of conduits, wherein said at least one heat exchanger and/or said plurality of conduits are in communication with said at least one wearable thermo-electric device.

24. The system of claim 1, wherein said at least one heat exchanger is at least one regenerative heat exchanger.

25. The system of claim 1, wherein said manifold is capable of being worn around the waist.

26. The system of claim 1, wherein said at least one blower comprises a feed blower and a return blower.

27. The system of claim 1, wherein said at least one member is a plurality of conduits, wherein said at least one heat exchanger and/or said plurality of conduits are in communication with said at least one wearable thermoelectric device.

28. The system of claim 1 further comprising a garment.

29. The system of claim 1, wherein said body temperature controlling system is configured to be worn about a movable area of a body and accommodates movement of the area of the body.

30. The system of claim 1, wherein said manifold further comprises at least one evaporative cooling device.

31. The system of claim 30, wherein said at least one evaporative cooling device provides evaporative cooling through the production of an aerosol of liquid droplets.

32. The system of claim 30, wherein said at least one evaporative cooling device comprises at least one nebulizer.

33. The system of claim 30, wherein said at least one heat exchanger is at least one regenerative heat exchanger.

34. The system of claim 1, further comprising a power source.

35. The system of claim 34, wherein said manifold further comprises said power source.

36. The system of claim 34, wherein said power source is a battery pack.

37. The system of claim 34 further comprising a controller for controlling gas flow.

\* \* \* \* \*